US008568466B2

(12) United States Patent
Shaolian et al.

(10) Patent No.: US 8,568,466 B2
(45) Date of Patent: Oct. 29, 2013

(54) GRAFT DEPLOYMENT SYSTEM

(75) Inventors: Samuel M. Shaolian, Newport Beach, CA (US); Gilbert Madrid, Laguna Niguel, CA (US); To Van Pham, Trabuco Canyon, CA (US); Trinh Van Pham, Santa Ana, CA (US)

(73) Assignee: Endologix, Inc., Irvine, CA (US)

( * ) Notice: Subject to any disclaimer, the term of this patent is extended or adjusted under 35 U.S.C. 154(b) by 200 days.

(21) Appl. No.: 13/269,332

(22) Filed: Oct. 7, 2011

(65) Prior Publication Data

US 2012/0029610 A1 Feb. 2, 2012

Related U.S. Application Data

(60) Division of application No. 10/722,367, filed on Nov. 25, 2003, now Pat. No. 8,034,100, which is a continuation-in-part of application No. 09/795,993, filed on Feb. 28, 2001, now Pat. No. 6,663,665, which is a division of application No. 09/266,661, filed on Mar. 11, 1999, now Pat. No. 6,261,316.

(60) Provisional application No. 60/429,666, filed on Nov. 26, 2002.

(51) Int. Cl.
*A61F 2/06* (2013.01)
(52) U.S. Cl.
USPC ............................................ 623/1.11
(58) Field of Classification Search
USPC .................. 606/108; 623/1.11, 1.12, 1.23
See application file for complete search history.

(56) References Cited

U.S. PATENT DOCUMENTS

| | | | | |
|---|---|---|---|---|
| 4,402,685 A | * | 9/1983 | Buhler et al. | 604/523 |
| 4,617,932 A | * | 10/1986 | Kornberg | 606/108 |
| 4,728,328 A | * | 3/1988 | Hughes et al. | 623/23.69 |
| 4,747,833 A | * | 5/1988 | Kousai et al. | 604/164.05 |
| 4,781,690 A | * | 11/1988 | Ishida et al. | 604/164.05 |
| 4,874,374 A | * | 10/1989 | Kousai et al. | 604/164.05 |
| 4,888,000 A | * | 12/1989 | McQuilkin et al. | 604/164.05 |
| 4,994,071 A | * | 2/1991 | MacGregor | 606/194 |
| 5,026,377 A | * | 6/1991 | Burton et al. | 606/108 |
| 5,104,388 A | * | 4/1992 | Quackenbush | 604/264 |
| 5,122,154 A | * | 6/1992 | Rhodes | 623/1.13 |
| 5,158,545 A | * | 10/1992 | Trudell et al. | 604/509 |
| 5,167,634 A | * | 12/1992 | Corrigan et al. | 604/160 |
| 5,242,399 A | * | 9/1993 | Lau et al. | 604/104 |
| 5,246,452 A | * | 9/1993 | Sinnott | 623/1.23 |
| 5,522,882 A | * | 6/1996 | Gaterud et al. | 623/1.11 |
| 5,545,209 A | * | 8/1996 | Roberts et al. | 623/1.11 |
| 5,571,135 A | * | 11/1996 | Fraser et al. | 623/1.12 |

(Continued)

*Primary Examiner* — Ryan Severson
(74) *Attorney, Agent, or Firm* — Knobbe Martens Olson & Bear LLP

(57) ABSTRACT

A method for deploying a bifurcated endoluminal prosthesis at the junction of a main vessel and first and second branch vessels, comprising providing a deployment system containing a prosthesis having a main body section and first and second proximally extending branch sections, introducing the deployment system into the first branch vessel at a first access site, advancing the deployment system distally through at least a portion of the first branch vessel and into the main vessel, releasing the second branch section of the prosthesis by proximally retracting an outer sheath of the deployment system, expanding the main body section of the prosthesis from a radially compressed state within the deployment system to a radially expanded state within the main vessel by removing a first peelable sheath from the main branch section, and expanding the second branch section within the second branch vessel by proximally retracting a second branch release wire.

11 Claims, 28 Drawing Sheets

(56) References Cited

U.S. PATENT DOCUMENTS

| | | | |
|---|---|---|---|
| 5,575,817 A * | 11/1996 | Martin | 623/1.35 |
| 5,591,226 A * | 1/1997 | Trerotola et al. | 623/1.12 |
| 5,591,228 A * | 1/1997 | Edoga | 128/898 |
| 5,607,445 A * | 3/1997 | Summers | 623/1.22 |
| 5,647,857 A * | 7/1997 | Anderson et al. | 604/264 |
| 5,669,924 A * | 9/1997 | Shaknovich | 623/1.11 |
| 5,720,735 A * | 2/1998 | Dorros | 604/284 |
| 5,733,267 A * | 3/1998 | Del Toro | 623/1.11 |
| 5,741,325 A * | 4/1998 | Chaikof et al. | 623/1.35 |
| 5,755,771 A * | 5/1998 | Penn et al. | 623/1.15 |
| 5,769,885 A * | 6/1998 | Quiachon et al. | 128/898 |
| 5,851,228 A * | 12/1998 | Pinheiro | 623/1.13 |
| 6,030,415 A * | 2/2000 | Chuter | 623/1.13 |
| 6,086,611 A * | 7/2000 | Duffy et al. | 623/1.35 |
| 6,143,016 A * | 11/2000 | Bleam et al. | 606/198 |
| 6,210,422 B1 * | 4/2001 | Douglas | 606/194 |
| 6,224,609 B1 * | 5/2001 | Ressemann et al. | 606/108 |
| 6,261,316 B1 * | 7/2001 | Shaolian et al. | 623/1.11 |
| 6,447,540 B1 * | 9/2002 | Fontaine et al. | 623/1.12 |
| 6,500,202 B1 * | 12/2002 | Shaolian et al. | 623/1.11 |
| 6,533,811 B1 * | 3/2003 | Ryan et al. | 623/1.23 |
| 6,827,731 B2 * | 12/2004 | Armstrong et al. | 623/1.12 |
| 6,899,727 B2 * | 5/2005 | Armstrong et al. | 623/1.12 |
| 6,939,327 B2 * | 9/2005 | Hall et al. | 604/164.05 |

* cited by examiner

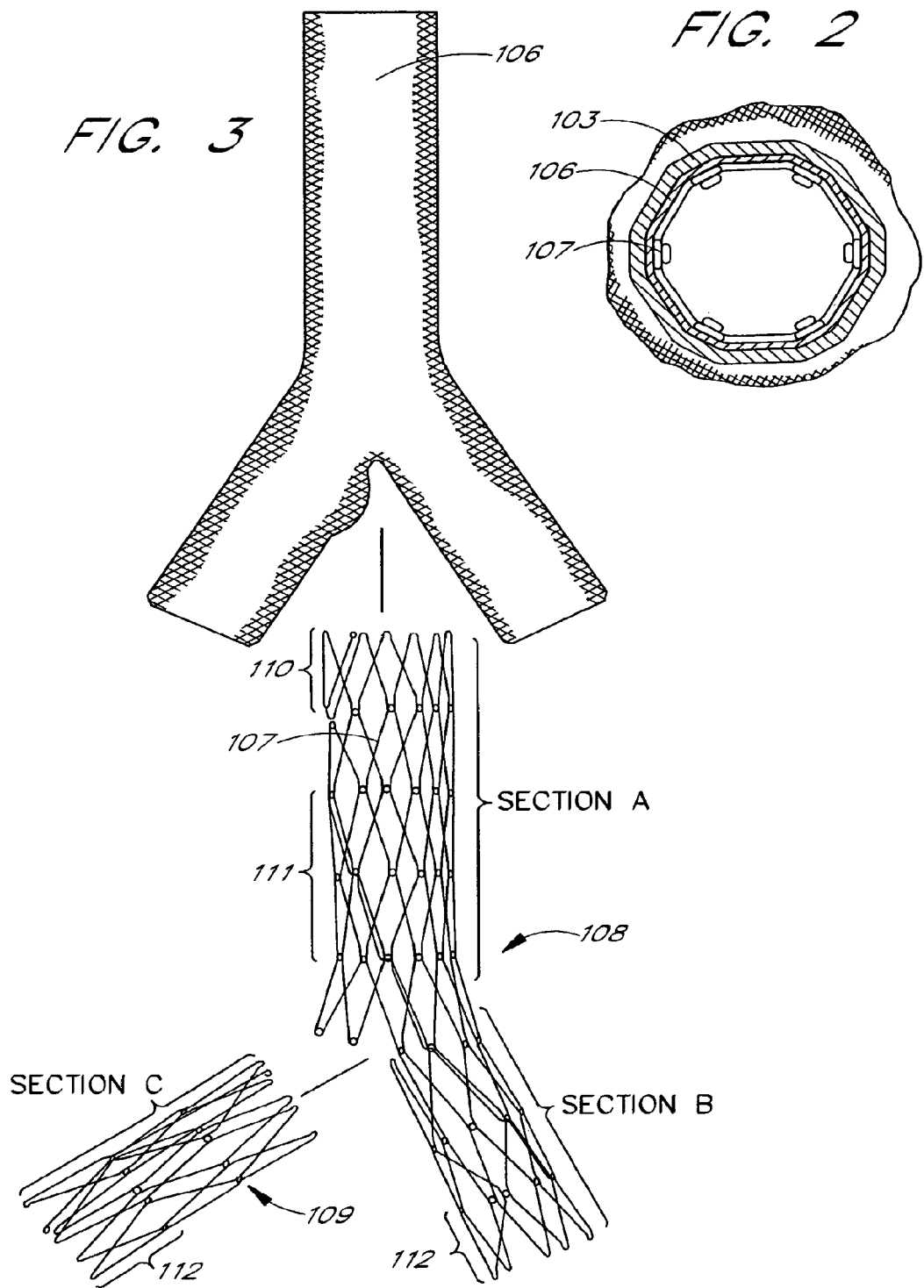

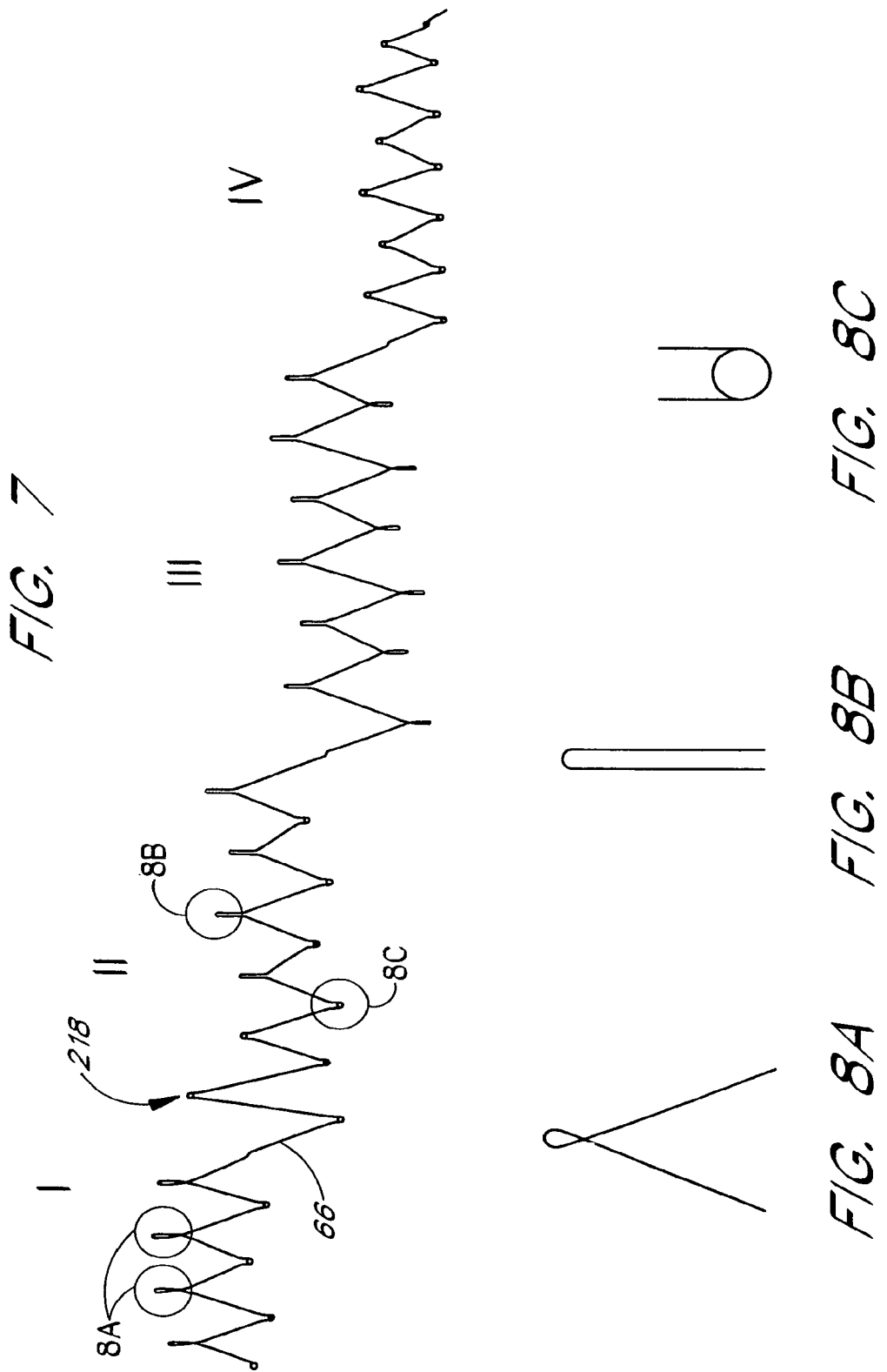

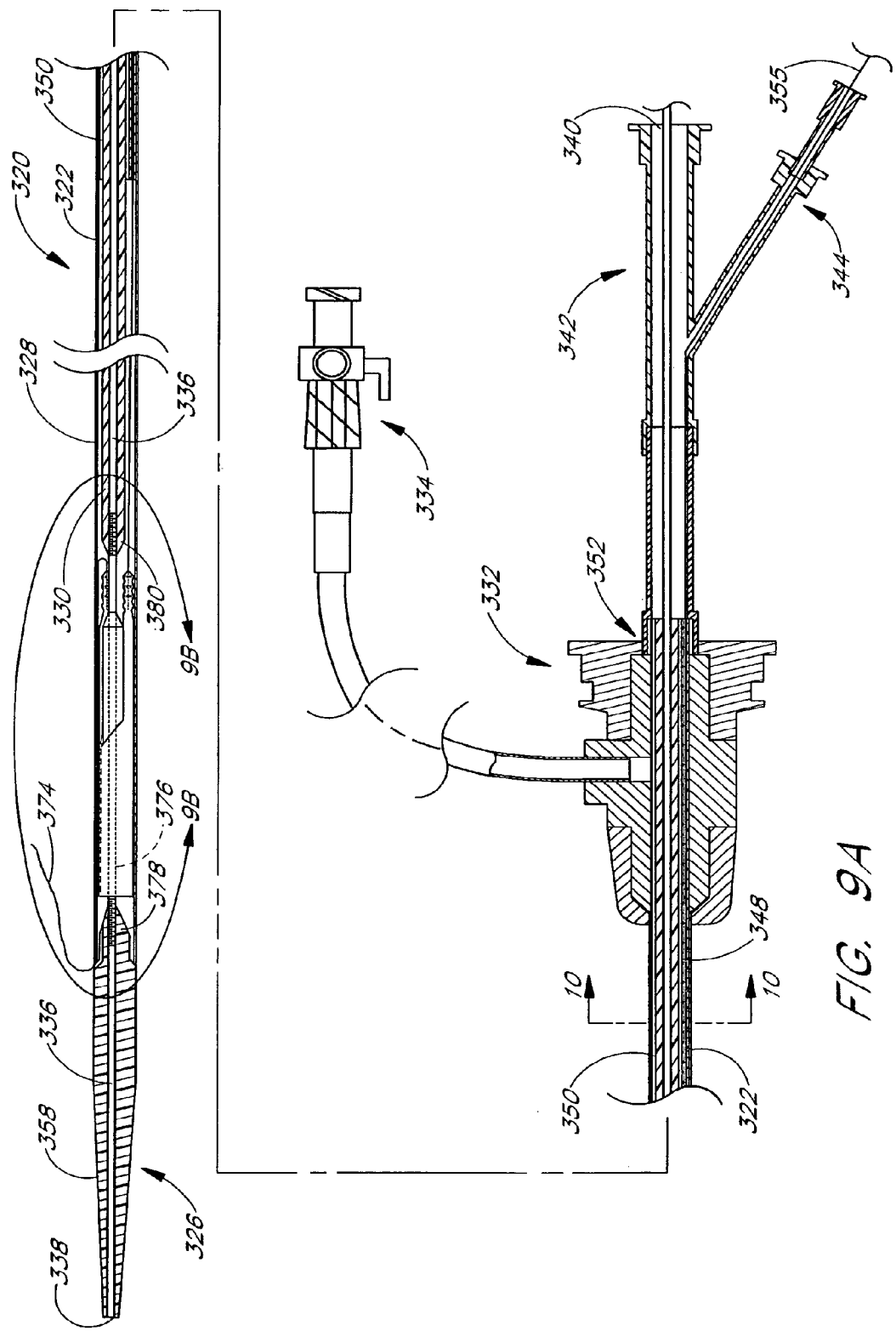

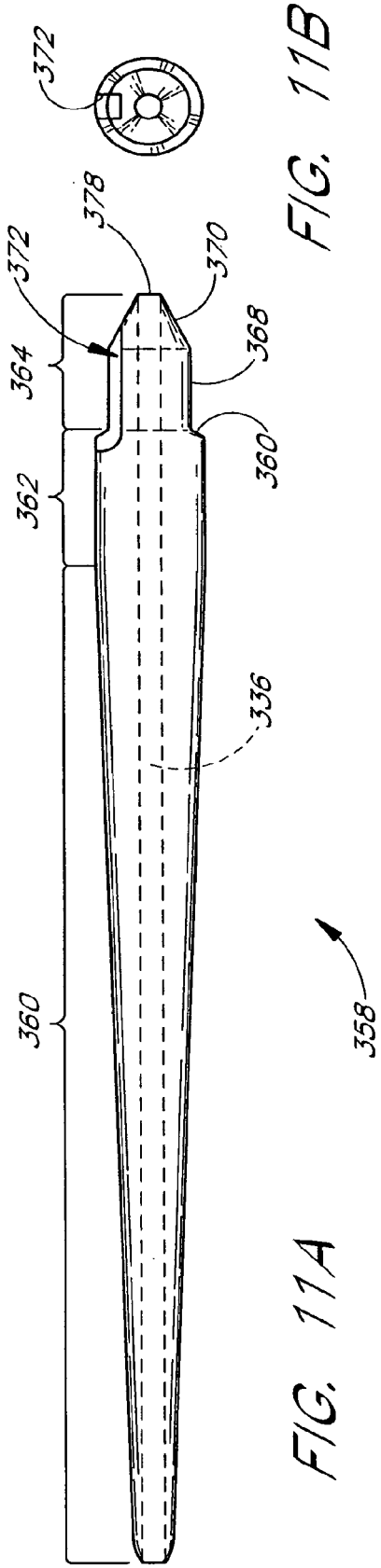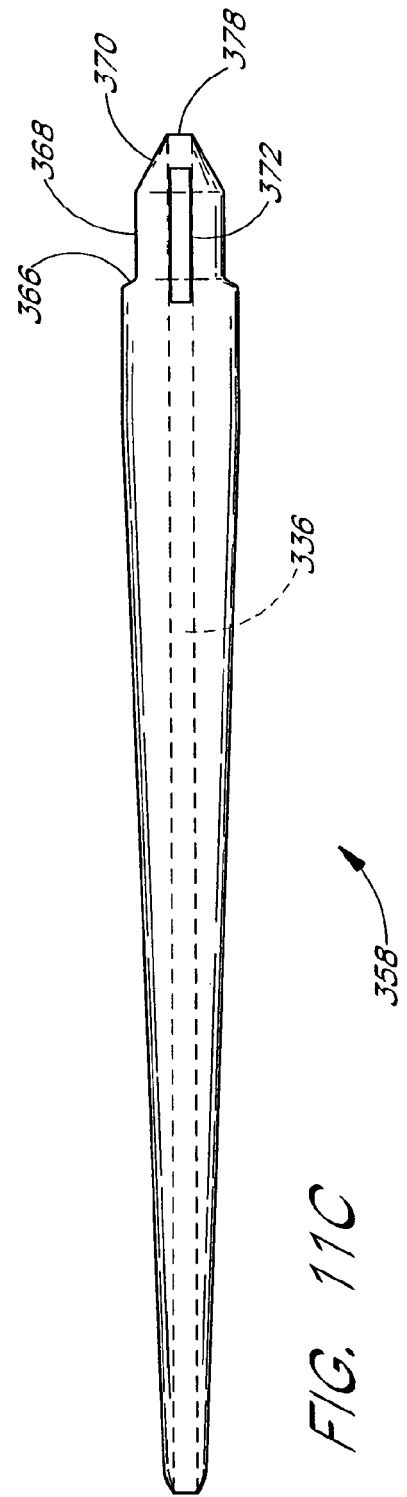

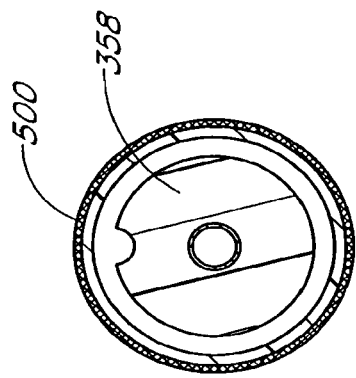
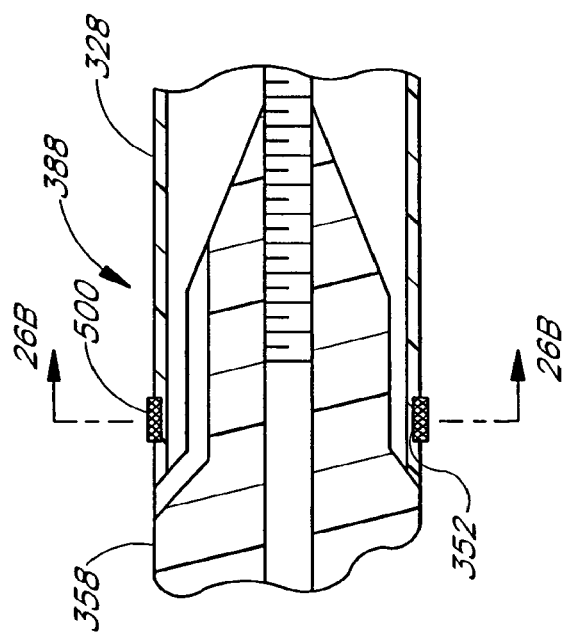

GRAFT DEPLOYMENT SYSTEM

PRIORITY INFORMATION AND INCORPORATION BY REFERENCE

This application is a divisional of U.S. patent application Ser. No. 10/722,367, filed Nov. 25, 2003, which is a continuation-in-part of U.S. patent application Ser. No. 09/795,993, filed Feb. 28, 2001, entitled "Singled Puncture Bifurcation Graft Deployment System", now U.S. Pat. No. 6,663,665, which is a divisional of U.S. patent application Ser. No. 09/266,661, filed Mar. 11, 1999, entitled "Singled Puncture Bifurcation Graft Deployment System", now U.S. Pat. No. 6,261,316, and claims the priority benefit under 35 U.S.C. §119(e) of Provisional Application 60/429,666 filed Nov. 26, 2002. Each of the above-listed applications is hereby incorporated by reference as if set forth herein in their entireties.

BACKGROUND OF THE INVENTION

Description of the Related Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON™, TEFLON™, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON™ tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery.

In general, transluminally implantable prostheses adapted for use in the abdominal aorta comprise a tubular wire cage surrounded by a tubular PTFE or Dacron sleeve. Both balloon expandable and self expandable support structures have been proposed. Endovascular grafts adapted to treat both straight segment and bifurcation aneurysms have also been proposed.

Notwithstanding the foregoing, there remains a need for a structurally simple, easily deployable transluminally implantable endovascular prosthesis, with a support structure adaptable to span either a straight or bifurcated abdominal aortic aneurysm. Preferably, the tubular prosthesis can be self expanded at the site to treat the abdominal aortic aneurysm, and exhibits flexibility to accommodate nonlinear anatomies and normal anatomical movement.

SUMMARY OF THE INVENTION

Accordingly, one embodiment a bifurcation graft deployment system, comprises an elongate, flexible catheter body, having a proximal end and a distal end and comprising an outer sheath and an inner core that is axially moveable with respect to the outer sheath. A main vessel graft restraint comprising a first peelable cover restrains a main vessel portion of a bifurcated graft. A first branch vessel graft restraint restrains a first branch vessel portion of the graft. A second branch vessel graft restraint restrains a second branch vessel portion of the graft. The first peelable cover is coupled to a main branch release element and wherein each of the main vessel graft restraint, first branch vessel graft restraint, and the second branch vessel graft restraint are positioned within the catheter body in a graft loaded condition.

Another embodiment comprises a method for deploying a bifurcated endoluminal prosthesis at the junction of a main vessel and first and second branch vessels. The method comprises providing a deployment system containing a prosthesis having a main body section and first and second proximally extending branch sections, introducing the deployment system into the first branch vessel at a first access site, advancing the deployment system distally through at least a portion of the first branch vessel and into the main vessel, releasing the second branch section of the prosthesis by proximally retracting an outer sheath of the deployment system, expanding the main body section of the prosthesis from a radially compressed state within the deployment system to a radially expanded state within the main vessel by removing a first peelable sheath from the main branch section, and expanding the second branch section within the second branch vessel by proximally retracting a second branch release wire.

Another embodiment involves deployment system for deploying a bifurcated prosthesis at the junction of a main vessel and first and second branch vessels. The system includes a delivery catheter having an inner core, an outer sheath and a distal tip that is coupled to the inner core, the inner core being slidably engaged within the outer sheath. A bifurcated prosthesis has a main body section with proximal and distal ends, and first and second branch sections at the proximal end of the main body section. The main body section is held in a radially compressed state by a first peelable cover. The first branch section is held in a radially compressed state within a first tubular cover and the second branch section is also held in a radially compressed within a second tubular cover.

Another embodiment involves a method for deploying a straight tube endoluminal prosthesis. The method comprises providing a deployment system containing a straight tube prosthesis including a distal section and a proximal section, introducing the deployment system into a vessel at an access site, advancing the deployment system distally through the vessel, proximally retracting an outer sheath of the deployment system to expose the prosthesis, and expanding at least a portion of the prosthesis from a radially compressed state within the deployment system to a radially expanded state within the vessel by proximately retracting a first release element so as to tear a peelable cover.

These embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 2 is a cross-sectional view of the implanted graft taken along the lines 2-2 of FIG. 1.

FIG. 3 is an exploded view of the bifurcated vascular prosthesis in accordance with the present invention, showing a two-part self expandable wire support structure separated from an outer tubular sleeve.

FIG. 7 is a plan view of formed wire useful for rolling about an axis to form a branch support structure in accordance with the three-part support embodiment of the present invention shown in FIG. 5.

FIGS. 8A, 8B and 8C are enlargements of the apexes delineated by lines A, B and C, respectively, in FIG. 7.

FIG. 9A is side elevational cross-section of a bifurcation graft delivery catheter in accordance with the present invention.

FIGS. 11A, B and C are side, top and rear views of a distal tip of the bifurcated delivery catheter shown in FIG. 9A.

FIG. 26A is a close view of portion 26A of FIG. 9B.

FIG. 26B is a cross-sectional view taken through line 26B-26B of FIG. 26A.

DETAILED DESCRIPTION OF THE PREFERRED EMBODIMENT

Figure 1:
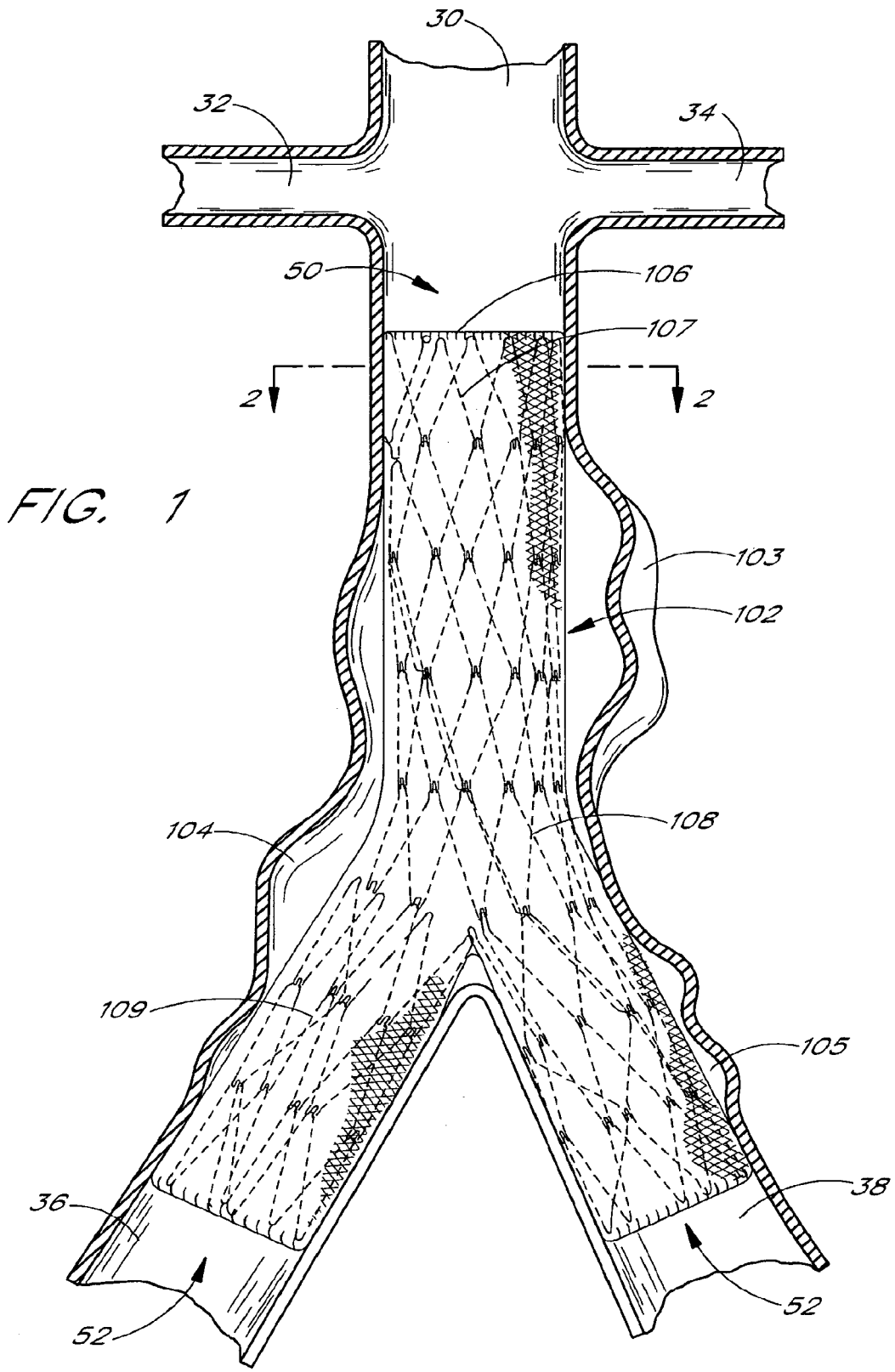
FIG. 1 is a schematic representation of a bifurcated vascular prosthesis in accordance with the present invention, positioned at the bifurcation between the abdominal aorta and the right and left common iliac arteries.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification.

An expanded bifurcated endoluminal vascular prosthesis 102, in accordance with one embodiment of the present invention, is illustrated spanning aneurysms 103, 104 and 105. It should be appreciated that the illustrated prosthesis 102 and the other prosthesis configurations disclosed herein are only examples of prostheses that are deployable using the devices and methods of the present invention. Moreover, as will be apparent to those of skill in the art in view of the disclosure herein, these devices and methods may be used to deploy essentially any self expandable bifurcated or straight segment prosthesis, The illustrated endoluminal vascular prosthesis 102 includes a polymeric sleeve 106 and a tubular wire support 107, illustrated in situ in FIG. 1. The sleeve 106 and wire support 107 are more readily visualized in the exploded view shown in FIG. 3. The endoluminal prosthesis 102 illustrated and described herein depicts an embodiment in which the polymeric sleeve 106 is situated concentrically outside of the tubular wire support 107. However, other embodiments may include a sleeve situated instead concentrically inside the wire support or on both of the inside and the outside of the wire support. Alternatively, the wire support may be embedded within a polymeric matrix or layer which makes up the sleeve. Regardless of whether the sleeve 106 is inside or outside the wire support 107, the sleeve may be attached to the wire support by any of a variety of means, as has been previously discussed.

The tubular wire support 107 comprises a primary component 108 for traversing the aorta and a first iliac, and a branch component 109 for extending into the second iliac. The primary component 108 may be formed from a continuous single length of wire, throughout both the aorta trunk portion and the iliac branch portion. See FIGS. 3 and 4. Alternatively, each iliac branch component can be formed separately from the aorta trunk portion. Construction of the graft from a three part cage conveniently facilitates the use of different gauge wire in the different components (e.g. 0.014" diameter main trunk and 0.012" diameter branch components).

Figure 4:
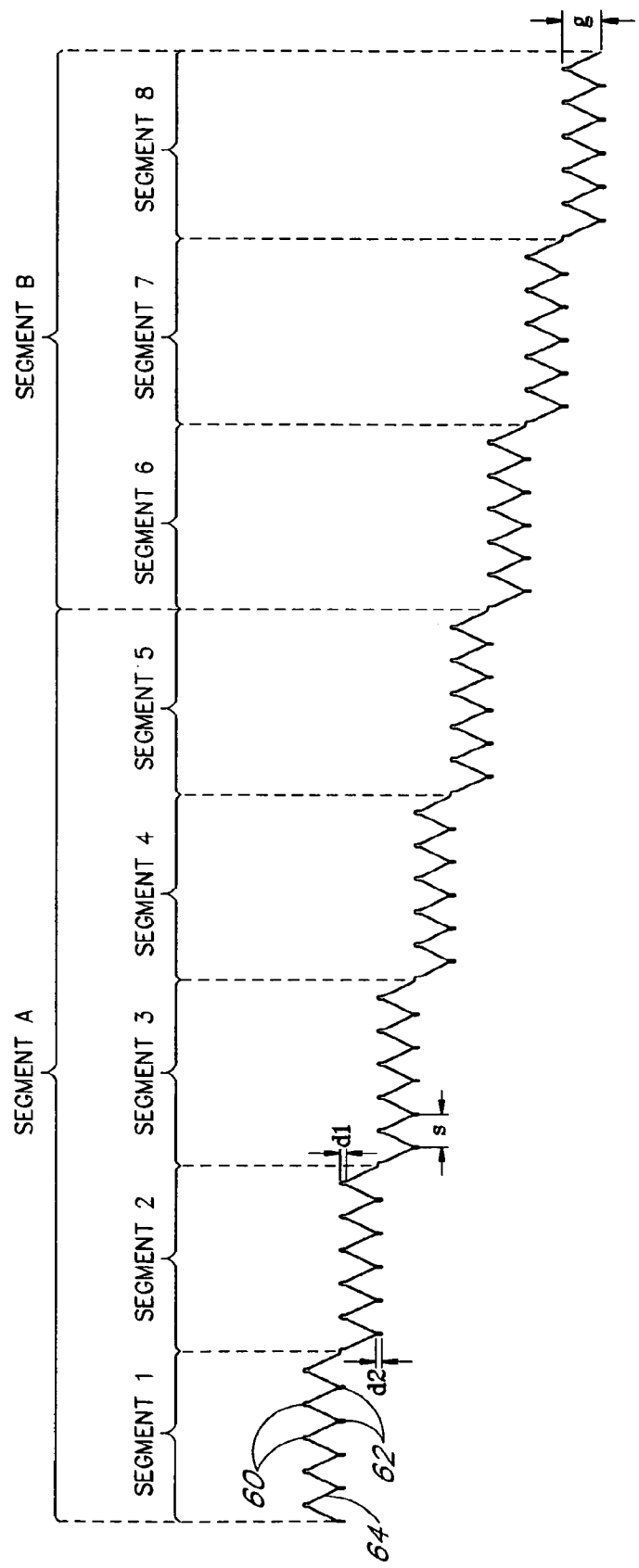
FIG. 4 is a plan view of formed wire useful for rolling about an axis into an aortic trunk segment and a first iliac branch segment support structure in accordance with the present invention.

The wire support 107 is preferably formed in a plurality of discrete segments, connected together and oriented about a common axis. In FIG. 4, Section A corresponds to the aorta trunk portion of the primary component 108, and includes segments 1-5. Segments 6-8 (Section B) correspond to the iliac branch portion of the primary component 108.

In general, each of the components of the tubular wire support 107 can be varied considerably in diameter, length, and expansion coefficient, depending upon the intended application. For implantation within a typical adult, the aorta trunk portion (section A) of primary component 108 will have a length within the range of from about 5 cm to about 12 cm, and, typically within the range of from about 9 cm to about 10 cm. The unconstrained outside expanded diameter of the section A portion of the primary component 108 will typically be within the range of from about 20 mm to about 40 mm. The unconstrained expanded outside diameter of the section A portion of primary component 108 can be constant or substantially constant throughout the length of section A, or can be tapered from a relatively larger diameter at the proximal end to a relatively smaller diameter at the bifurcation. In general, the diameter of the distal end of section A will be on the order of no more than about 95% and, preferably, no more than about 85% of the diameter of the proximal end of section A.

The right and left iliac portions, corresponding to section B on primary component 108 and section C will typically be bilaterally symmetrical. Section C length will generally be within the range of from about 1 cm to about 5 cm, and section C diameter will typically be within the range of from about 10 mm to about 20 mm.

Referring to FIG. 3, the wire cage 107 is dividable into a proximal zone 110, a central zone 111 and a distal zone 112. In addition, the wire cage 107 can have a transitional tapered and or stepped diameter within a given zone. Further details of the bifurcated and straight segment grafts in accordance with the present invention are disclosed in copending U.S. patent application Ser. No. 09/251,363 filed Feb. 17, 1999 and entitled Articulated Bifurcation Graft, the disclosure of which is incorporated in its entirety herein by reference.

Referring to FIG. 4, there is illustrated a plan view of the single formed wire used for rolling about a longitudinal axis to produce a primary segment 108 having a five segment aorta section and a three segment iliac section. The formed wire exhibits distinct segments, each corresponding to an individual tubular segment in the tubular support. Additional details of the wire cage layout and construction can be found in copending U.S. patent application Ser. No. 09/034,689 entitled Endoluminal Vascular Prosthesis, filed Mar. 4, 1998, the disclosure of which is incorporated in its entirety herein by reference.

Each segment has a repeating pattern of proximal bends 60 connected to corresponding distal bends 62 by wall sections 64 which extend in a generally zig-zag configuration when the segment is radially expanded. Each segment is connected to the adjacent segment through a connector 66, and one or more links 70 (see FIG. 6). The connector 66 in the illustrated embodiment comprises two wall sections 64 which connect a proximal bend 60 on a first segment with a distal bend 62 on a second, adjacent segment. The connector 66 may additionally be provided with a connector bend 68, which may be used to impart increased radial strength to the graft and/or provide a tie site for a circumferentially extending suture.

In the illustrated embodiment, section A is intended for deployment within the aorta whereas section B is intended to be deployed within a first iliac. Thus, section B will preferably have a smaller expanded diameter than section A. This may be accomplished by providing fewer proximal and distal bends 60, 62 per segment in section B or in other manners as will be apparent to those of skill in the art in view of the disclosure herein. In the illustrated embodiment, section B has one fewer proximal bend 60 per segment than does each segment in section A. This facilitates wrapping of the wire into a tubular prosthesis cage such as that illustrated in FIG. 3, so that the iliac branch has a smaller diameter than the aorta branch. At the bifurcation, an opening remains for connection of the second iliac branch. The second branch is preferably formed from a section of wire in accordance with the general principles discussed above, and in a manner that produces a similarly dimensioned wire cage as that produced by section B. The second iliac branch (section C) may be attached at the bifurcation to section A and/or section B in any of a variety of manners, to provide a secure junction therebetween. In one embodiment, one or two of the proximal bends 60 on section C will be secured to the corresponding distal bends 62 on the distal most segment of section A. Attachment may be accomplished such as through the use of a circumferentially threaded suture, through links 70 as has been discussed previously, through soldering or other attachment means. The attachment means will be influenced by the desired flexibility of the graft at the bifurcation, which will in turn be influenced by the method of deployment of the vascular graft as will be apparent to those of skill in the art in view of the disclosure herein.

Figure 5:
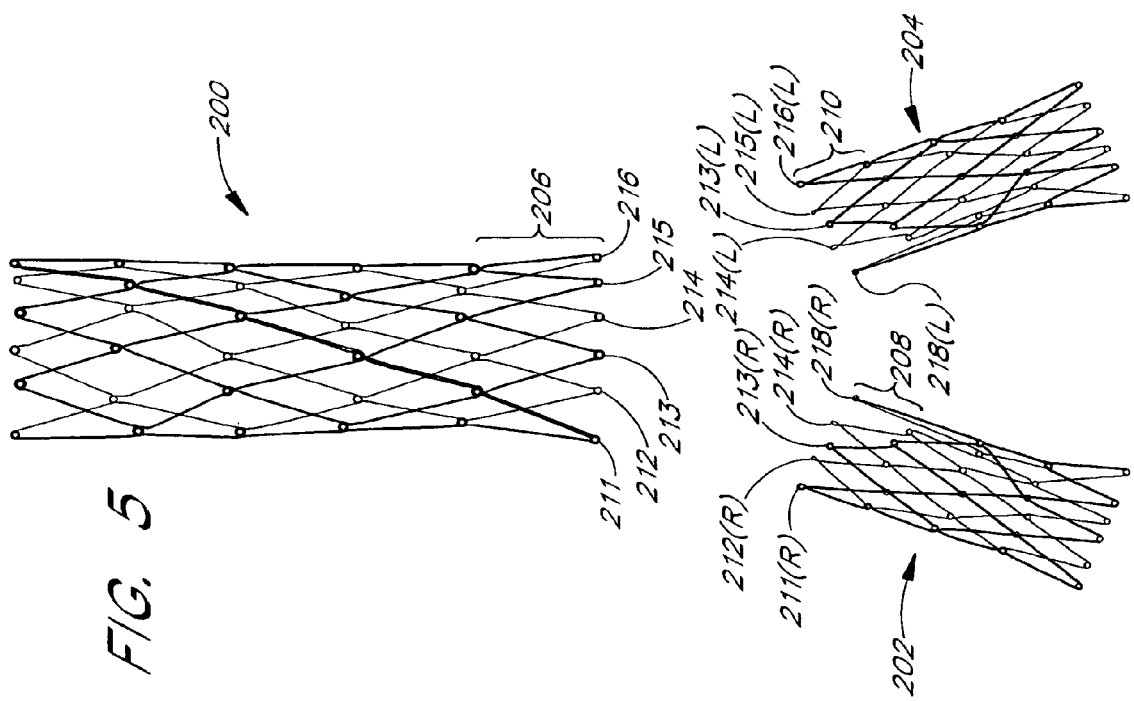
FIG. 5 is a schematic representation of another embodiment of the wire support structure for the bifurcated vascular prosthesis of the present invention, showing a main body support structure and separate branch support structures.

Referring to FIG. 5, there is disclosed an exploded schematic representation of a hinged or articulated variation in the tubular wire support structure for a bifurcated graft in accordance with present invention. The tubular wire support comprises a main body, or aortic trunk portion 200 and right 202 and left 204 iliac branch portions. Right and left designations correspond to the anatomic designations of right and left common iliac arteries. The proximal end 206 of the aortic trunk portion 200 has apexes 211-216 adapted for connection with the complementary apexes on the distal ends 208 and 210 of the right 202 and left 204 iliac branch portions, respectively. Complementary pairing of apexes is indicated by the shared numbers, wherein the right branch portion apexes are designated by (R) and the left branch portion apexes are designated by (L). Each of the portions may be formed from a continuous single length of wire. See FIG. 7.

Figure 6:
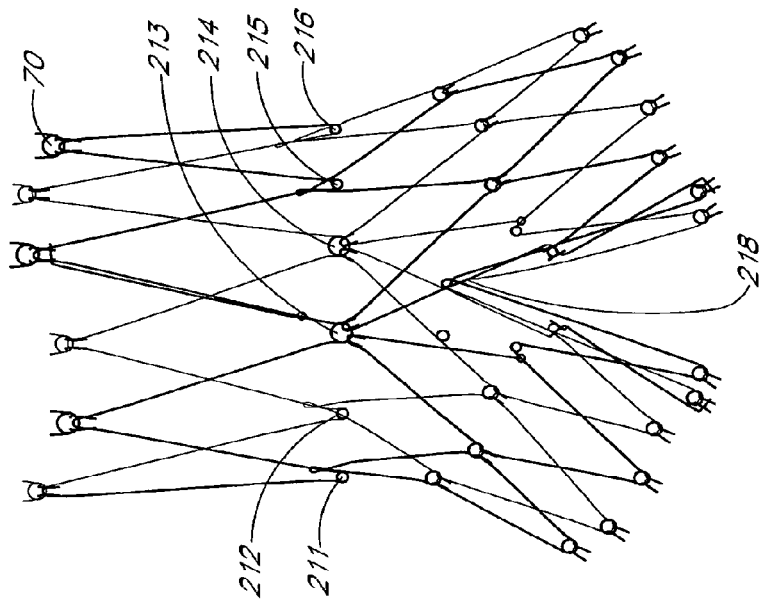
FIG. 6 is a schematic representation of the three-part wire support structure as in FIG. 5, illustrating the sliding articulation between the branch supports and the main body support.

Referring to FIG. 6, the assembled articulated wire support structure is shown. The central or medial apex 213 in the foreground (anterior) of the aortic trunk portion 200 is linked with 213(R) on the right iliac portion 202 and 213(L) on the left iliac portion 204. Similarly, the central apex 214 in the background (posterior) is linked with 214(R) on the right iliac portion 202 and 214(L) on the left iliac portion 204. Each of these linkages has two iliac apexes joined with one aortic branch apex. The medial most apexes 218 (R) and (L) of the iliac branch portions 202 and 204 are linked together, without direct connection with the aortic truck portion 200.

The medial apexes 213 and 214 function as pivot points about which the right and left iliac branches 202, 204 can pivot to accommodate unique anatomies. Although the right and left iliac branches 202, 204 are illustrated at an angle of about 45° to each other, they are articulable through at least an angle of about 90° and preferably at least about 120°. The illustrated embodiment allows articulation through about 180° while maintaining patency of the central lumen. To further improve patency at high iliac angles, the apexes 213 and 214 can be displaced proximally from the transverse plane which roughly contains apexes 211, 212, 215 and 216 by a minor adjustment to the fixture about which the wire is formed. Advancing the pivot point proximally relative to the lateral apexes (e.g., 211, 216) opens the unbiased angle between the iliac branches 202 and 204.

In the illustrated embodiment, the pivot point is formed by a moveable link between an eye on apex 213 and two apexes 213R and 213L folded therethrough. To accommodate the two iliac apexes 213R and 213L, the diameter of the eye at apex 213 may be slightly larger than the diameter of the eye on other apexes throughout the graft. Thus, for example, the diameter of the eye at apex 213 in one embodiment made from 0.014" diameter wire is about 0.059", compared to a diameter of about 0.020" for eyes elsewhere in the graft.

Although the pivot points (apexes 213, 214) in the illustrated embodiment are on the medial plane, they may be moved laterally such as, for example, to the axis of each of the iliac branches. In this variation, each iliac branch will have an anterior and a posterior pivot link on or about its longitudinal axis, for a total of four unique pivot links at the bifurcation. Alternatively, the pivot points can be moved as far as to lateral apexes 211 and 216. Other variations will be apparent to those of skill in the art in view of the disclosure herein.

To facilitate lateral rotation of the iliac branches 202, 204 about the pivot points and away from the longitudinal axis of the aorta trunk portion 200 of the graft, the remaining links between the aorta trunk portion 200 and the iliac branches 202, 204 preferably permit axial compression and expansion. In general, at least one and preferably several links lateral to the pivot point in the illustrated embodiment permit axial compression or shortening of the graft to accommodate lateral pivoting of the iliac branch. If the pivot point is moved laterally from the longitudinal axis of the aorta portion of the graft, any links medial of the pivot point preferably permit axial elongation to accommodate lateral rotation of the branch. In this manner, the desired range of rotation of the iliac branches may be accomplished with minimal deformation of the wire, and with patency of the graft optimized throughout the angular range of motion.

To permit axial compression substantially without deformation of the wire, the lateral linkages, 211 and 212 for the right iliac, and 215 and 216 for the left iliac, may be different from the previously described apex-to-apex linkage configurations. The lateral linkages are preferably slideable linkages, wherein a loop formed at the distal end of the iliac apex slidably engages a strut of the corresponding aortic truck portion. The loop and strut orientation may be reversed, as will be apparent to those of skill in the art. Interlocking "elbows" without any distinct loop may also be used. Such an axially compressible linkage on the lateral margins of the assembled wire support structure allow the iliac branch portions much greater lateral flexibility, thereby facilitating placement in patients who often exhibit a variety of iliac branch asymmetries and different angles of divergence from the aortic trunk.

Referring to FIG. 7, there is illustrated a plan view of a single formed wire used for rolling about a longitudinal axis to produce a four segment straight tubular wire support for an iliac limb. The formed wire exhibits distinct segments, each corresponding to an individual tubular segment in the tubular supports 202 or 204 (See FIG. 5). The distal segment I, is adapted to articulate with the aortic trunk portion 200 and the adjacent iliac limb portion. The distal segment (I) has two apexes (e.g. corresponding to 211 and 212 on the right iliac portion 202 in FIG. 5) which form a loop adapted to slidably engage a strut in the lateral wall of the aortic portion. These articulating loops (A) are enlarged in FIG. 8A. As discussed above, the loops are preferably looped around a strut on the corresponding apex of the proximal aortic segment to provide a sliding linkage.

The apex 218 is proximally displaced relative to the other four apexes in the distal segment (I). Apex 218 (R or L) is designed to link with the complementary 218 apex on the other iliac branch portion (See FIG. 6). The apex 218 in the illustrated embodiment is formed adjacent or near an inter-segment connector 66, which extends proximally from the distal segment.

The other apexes on the distal segment (I) of an iliac limb are designed to link with a loop on the corresponding apex of the proximal aortic segment. Because many variations of this linkage are consistent with the present invention the form of the corresponding apexes may vary. In a preferred variation, the apexes (B) form a narrow U-shape, having an inside diameter of about 0.019 inches in an embodiment made from 0.012 inch Conichrome wire (tensile strength 300 ksi minimum) as illustrated in FIG. 8B. The U-shaped, elongated axial portion of the apex shown in FIG. 8B permits the apex to be wrapped through and around a corresponding loop apex of the proximal aortic segment.

In more general terms, the wire support illustrated in FIGS. 5 and 6 comprises a main body support structure formed from one or more lengths of wire and having a proximal end, a distal end and a central lumen extending along a longitudinal axis. The wire support also comprises a first branch support structure formed from one or more lengths of wire and having a proximal end, a distal end and a central lumen therethrough. The first branch support structure is pivotably connected to the proximal end of the main body support structure. The tubular wire support further comprises a second branch support structure formed from one or more lengths of wire and having a proximal end, a distal end and a central lumen extending therethrough. The distal end of the second branch support structure is pivotably connected to the proximal end of the main body support structure.

Further, the distal ends of the first and second branch structures may be joined together by a flexible linkage, formed for example between apexes 218(R) and 218(L) in FIG. 5. By incorporating a medial linkage between the two branch support structures and pivotable linkages with the main trunk, the first and second branch support structures can hinge laterally outward from the longitudinal axis without compromising the volume of the lumen. Thus, the branches may enjoy a wide range of lateral movement, thereby accommodating a variety of patient and vessel heterogeneity. Additional corresponding apexes between the main trunk and each iliac branch may also be connected, or may be free floating within the outer polymeric sleeve. Axially compressible lateral linkages, discussed above and illustrated in FIG. 6, may optionally be added.

The proximal apexes (C) of the iliac limb portions are adapted to link with the distal apexes of the next segment. These proximal apexes preferably form loops, such as those illustrated in FIG. 8C, wherein the elongated axial portions of the corresponding proximal apex in the adjacent segment can wrap around the loop, thereby providing flexibility of the graft.

The wire may be made from any of a variety of different alloys and wire diameters or non-round cross-sections, as has been discussed. In one embodiment of the bifurcation graft, the wire gauge remains substantially constant throughout section A of the primary component 49 and steps down to a second, smaller cross-section throughout section B of primary component 108.

A wire diameter of approximately 0.018 inches may be useful in the aorta trunk portion of a graft having five segments each having 2.0 cm length per segment, each segment having six struts intended for use in the aorta, while a smaller diameter such as 0.012 inches might be useful for segments of the graft having 6 struts per segment intended for the iliac artery.

In one embodiment of the present invention, the wire diameter may be tapered throughout from the proximal to distal ends of the section A and/or section B portions of the primary component 108. Alternatively, the wire diameter may be tapered incremental or stepped down, or stepped up, depending on the radial strength requirements of each particular clinical application. In one embodiment, intended for the abdominal aortic artery, the wire has a cross-section of about 0.018 inches in the proximal zone 110 and the wire tapers down regularly or in one or more steps to a diameter of about 0.012 inches in the distal zone 112 of the graft 102. End point dimensions and rates of taper can be varied widely, within the spirit of the present invention, depending upon the desired clinical performance.

In general, in the tapered or stepped wire embodiments, the diameter of the wire in the iliac branches is no more than about 80% of the diameter of the wire in the aortic trunk. This permits increased flexibility of the graft in the region of the iliac branches, which has been determined by the present inventors to be clinically desirable.

The collapsed prosthesis in accordance with the present invention has a diameter in the range of about 2 mm to about 10 mm. Preferably, the maximum diameter of the collapsed prosthesis is in the range of about 3 mm to 6 mm (12 to 18 French). Some embodiments of the delivery catheter including the prosthesis will be in the range of from 18 to 20 or 21 French; other embodiments will be as low as 19 F, 16 F, 14 F, or smaller. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

A deployment catheter 320 for deploying a self expandable bifurcation graft such as the one described above and having certain features and aspects according to the present invention will now be described with initial reference to FIGS. 9A-9C.

The deployment catheter 320 comprises an elongate flexible multicomponent tubular body 322 having a proximal end 324 and a distal end 326. The tubular body 322 and other components of this catheter 320 can be manufactured in accordance with any of a variety of techniques well known in the catheter manufacturing field. Suitable materials and dimensions can be readily selected taking into account the natural anatomical dimensions in the iliacs and aorta, together with the dimensions dictated by the desired percutaneous access site.

The elongate flexible tubular body 322 comprises an outer sheath 328, which is axially movably positioned upon a central tubular core 330. In one embodiment, the outer sheath 328 comprises extruded PTFE and/or PEEK, having an outside diameter of about 0.280" and an inside diameter of about 0.250". The outer sheath 328 preferably has an axial length within the range of from about 40" to about 55", and, in one embodiment of the catheter 320 having an overall length of 110 cm, the axial length of the outer sheath 328 is about 52". Preferably, the outer sheath 328 is provided at its proximal end with a manifold 332, having a hemostatic valve 334 thereon and access ports such as for the infusion of drugs or contrast media as will be understood by those of skill in the art.

The central core 330 defines, in part, a central guidewire lumen 336, which may in an over the wire construction extend throughout the length of catheter 320. The central lumen 336 has a distal exit port 338 and a proximal access port 340 as will be understood by those of skill in the art. As best seen in FIG. 9A, in the illustrated embodiment, the proximal access port 340 is defined by a backend connector 342, which is attached to the proximal end of the central core 330. The illustrated backend connector 342 preferably also defines a release wire port 344, the utility of which will be described below.

In a preferred embodiment, the central core 330 is axially movably positioned within but rotationally locked to the outer sheath 328. As such, the rotational orientation of the central core 330 remains fixed with respect to the rotational orientation of the outer sheath 328. Rotational engagement can be accomplished in any of a variety of ways, normally involving complementary surface structures such as keys or splines on the associated components. For example, the central core 330 can be provided with one or two or more radially outwardly extending projections, along a portion or all of its axial length. This projection is slidably received within a radially outwardly extending slot on the interior surface of the outer sheath 328, or a component secured thereto. Alternatively, a radially inwardly extending projection on the outer sheath 328 or an associated component can be received with an axially extending recess on the outer surface of the central core 330. Alternatively, any of a variety of non-round configurations for the central core 330 such as elliptical, oval, triangular, square, polygonal, and the like, can be slidably received within a complementary-shaped aperture on or connected to the outer sheath 328.

Figure 10:
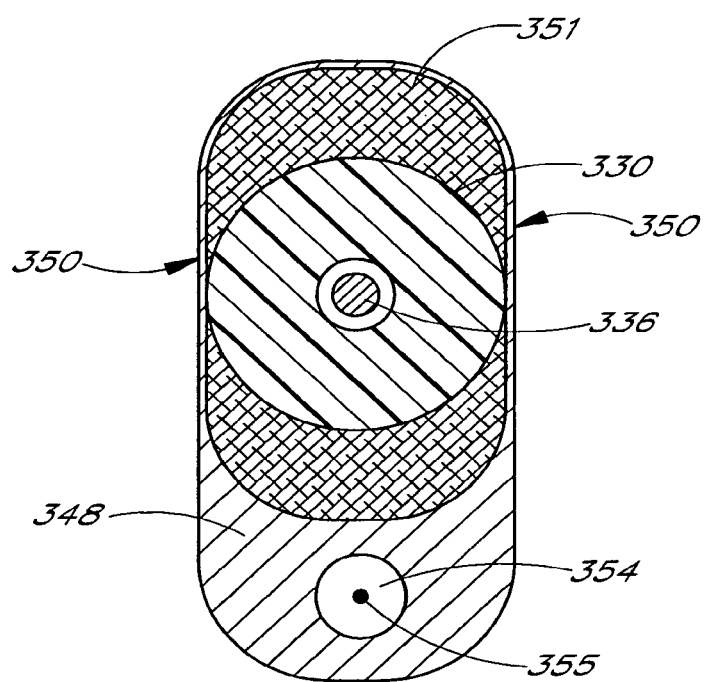
FIG. 10 is a cross-section taken along the line 10-10 in FIG. 9A.

In the illustrated embodiment, the central core 330 is provided with a proximal stiffening element 348 (see also FIG. 10), which may be in the form of a stainless steel hypotube with a non-round cross-section with two opposing flat sides 350 extending axially along its length. See FIG. 10. The illustrated stiffening element 348 is coupled to the central core 330 by an adhesive, such as, for example, an epoxy 351. A corresponding aperture is provided in a rotational lock 352 provided on the manifold 332. The resulting assembly enables rotation of the manifold 334 to cause a commensurate rotation of the central core 330. Specific dimensions and design details of the rotational lock 352 disclosed herein will be readily apparent to those of skill in the art in view of the disclosure herein. As shown in FIG. 10, the proximal stiffening element 348 preferably also defines a release wire lumen 354 for guiding a release wire 355 to the release wire port 344.

A distal segment of the deployment catheter 320 comprises an elongate flexible tapered distal tip 358. With particular reference to FIGS. 11A-C, the illustrated distal tip 358 includes a tapered portion 360, a first cylindrical portion 362 and a recessed portion 364. In one embodiment of the deployment catheter 320, the distal tip 358 has an axial length of approximately 73 millimeters. In such an embodiment, the tapered portion 360 has an axial length of approximately 48 millimeters, the first cylindrical portion 362 has an axial length of approximately 15 millimeters and the recessed portion 364 has an axial length of approximately 10 millimeters. However, it should be appreciated the length of the distal tip 358 and the length of the portions 360, 362, 364 can be varied depending upon the desired trackability and flexibility characteristics.

Preferably, the first cylindrical portion 362 has an outside diameter that is approximately equal to the outside diameter of the outer sheath 328. The tapered portion 360, in turn, preferably tapers from an outside diameter that is approximately equal to the outside diameter of the first cylindrical portion 362 to an outside diameter that is at least about 50% smaller at the distal end thereof.

In a preferred embodiment, the recessed portion 364 is configured to fit within the distal end of the outer sheath 328. In the illustrated embodiment, the recessed portion 364 preferably defines an annular shoulder 366, which prevents distal movement of the outer sheath 328 with respect to the distal tip 358. The illustrated recessed portion 364 also includes a second cylindrical portion 368 and a tapered proximal portion 370. The second cylindrical portion 368 is configured to fit within the distal end of the outer sheath 328 when the catheter 320 is in a loaded configuration. See FIG. 9B. Preferably, the second cylindrical portion 368 has an outer diameter that is slightly smaller than the inner diameter of the distal end of the outer sheath 328. The tapered portion 370 has a outer diameter that tapers in the proximal direction and terminates at the central lumen 336, which extends through the distal tip 358 from the proximal end to the distal end.

The distal tip preferably also includes a groove 372, which in the illustrated embodiment extends axially along the second cylindrical portion 368, through the annual shoulder 366 and the proximal end of the first cylindrical portion 362. As best seen in FIG. 9B, in a loaded configuration, the groove 372 provides a path for a contralateral guidewire 374, the utility of which will be described below.

Figure 12:
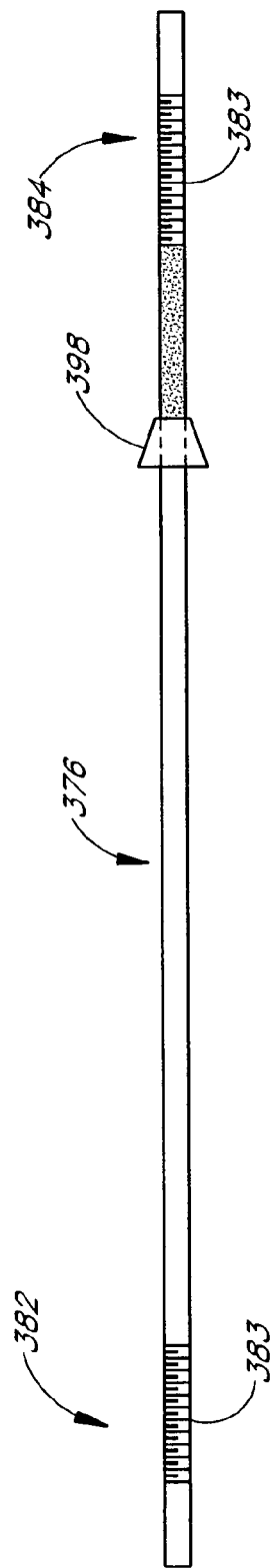
FIG. 12 is a side elevational view of a distal hypotube of the bifurcated delivery catheter shown in FIG. 9A.

The distal tip 358 is preferably coupled to the central core 330. In the illustrated embodiment, the distal tip 358 is coupled to the central core 30 through a distal hypotube 376, which is best seen in FIG. 12. The distal hypotube 376 may comprise a solid wall such as stainless steel, or a more flexible wall such as a braided polymide tubing. Preferably, the polyimide tubing has an inside diameter of about 0.059" and an outside diameter that is slight smaller than the diameter of the central lumen 336 at a proximal end 378 of the distal tip 358 and a distal end 380 of the central core 330. See FIG. 9B. An internal braid is may be made from 0.0015" stainless steel 304 wire at a pic count of about 50 braids per inch, such as may be obtained from Phelps Dodge (GA) or H.V. Technologies (GA). The use of flexible tubing such as spiral cut layers or woven or braided tubing in place of conventional stainless steel or other metal hypotubing increases the lateral flexibility of the assembled device, which facilitates the placement and deployment steps.

In the embodiment illustrated in FIG. 12, a distal end 382 of the hypotube 376 is frictionally fitted within the proximal end 378 of the distal tip 358. To aid the frictional fit, the distal end 382 is may be provided with a one or more ridges or grooves 383. In a similar manner, a proximal end 384 of the distal hypotube 376 is frictionally fitted within the distal end 380 of the central core 330. The proximal end 384 of the distal hypotube 376 may also be provided with one or more ridges or grooves 383. In other embodiments, the distal hypotube 376 can be connected to distal tip 358 and/or the central core 330 by thermal bonding, adhesive bonding, and/or any of a variety of other securing techniques known in the art which can also be used in addition to the frictional fit described above.

Figure 9B:
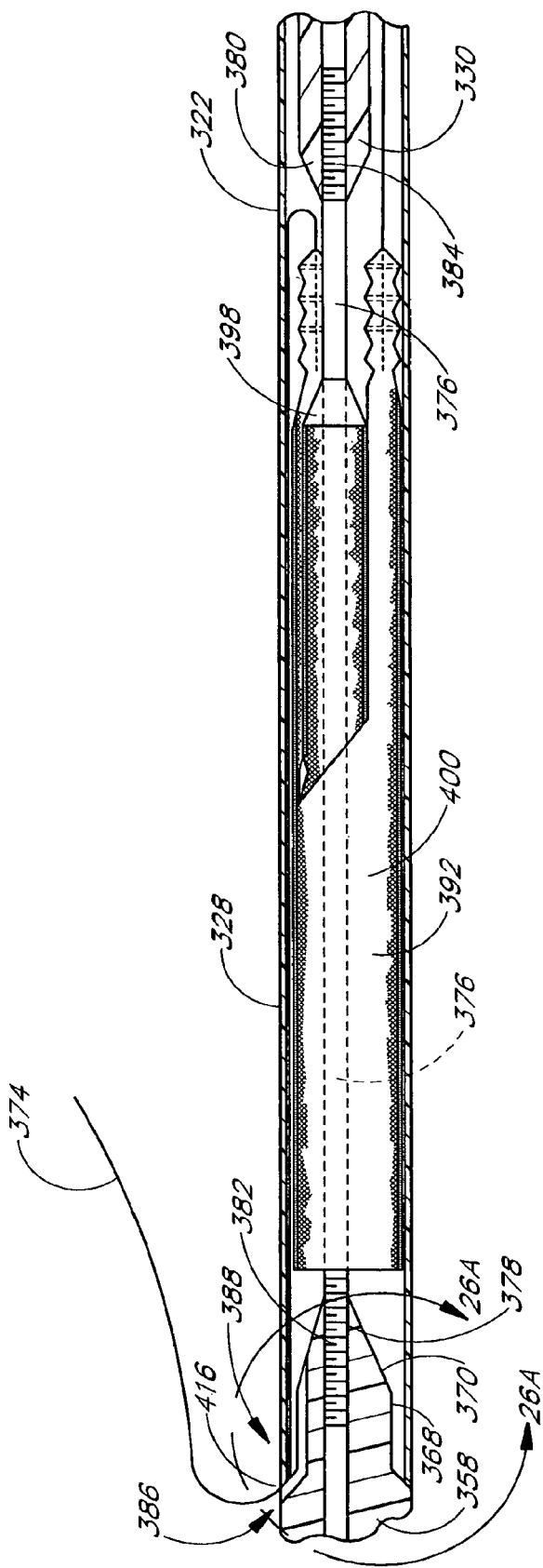
FIG. 9B is a closer view of a portion of FIG. 9A.

As can be seen from FIG. 9B, in a loaded configuration, a junction 386 is formed between a distal end 388 of the outer sheath 328 and the distal tip 358. As can be seen in FIG. 9C, proximal retraction of the outer sheath 328 with respect to the central core 330 will expose a bifurcated endoluminal graft 390, as will be discussed in more detail below.

Figure 9C:
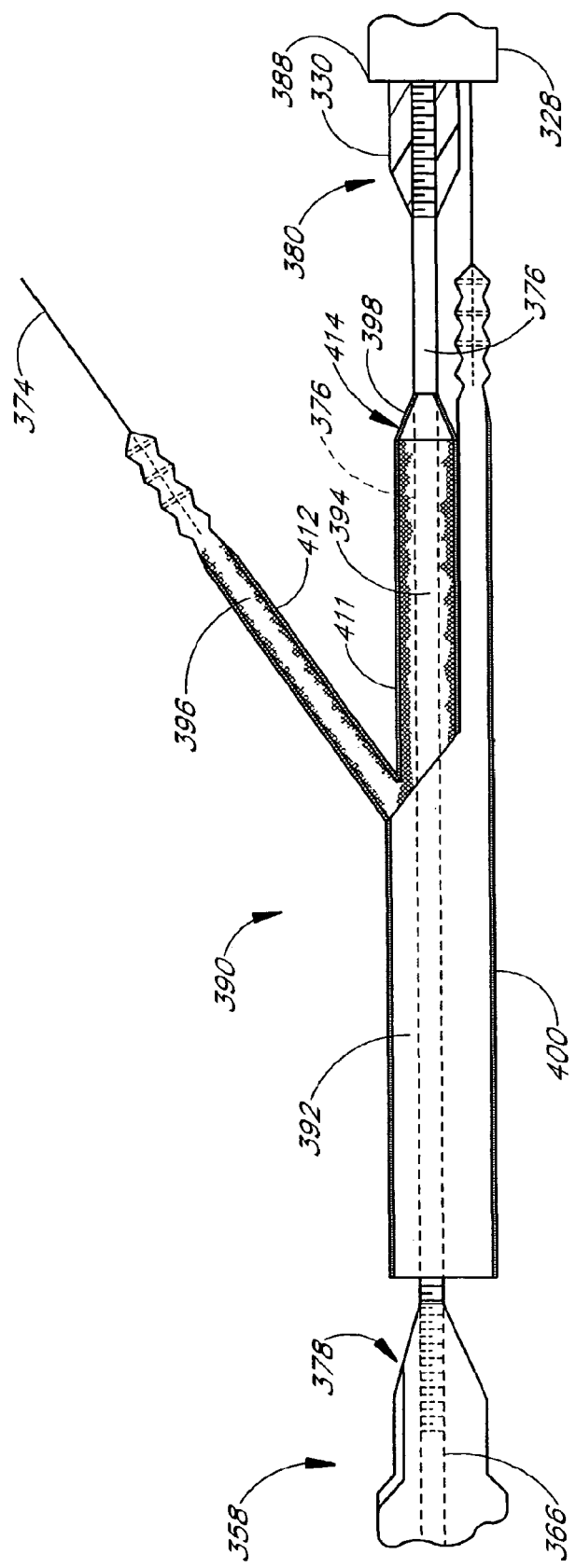
FIG. 9C is similar to the view shown in FIG. 9B with the bifurcation graft delivery catheter shown in a stent exposed configuration.

With continued reference to FIG. 9C, the bifurcated endoluminal graft 390 is illustrated in an exposed configuration. The graft 390 comprises aortic trunk portion 392, a proximal ipsilateral iliac branch 394, and a proximal contralateral iliac branch 396. In the loaded configuration (see FIG. 9B), the graft 390 is contained within the outer tubular sheath 328 between the proximal end of the distal tip 358 and the distal end 380 of the central core 330. Proximal movement of the graft 390 is prevented by a proximal stop 398, which is axially immovably connected to the distal hypotube 376. See also FIG. 12. The function of the proximal stop 398 can be accomplished through any of a variety of structures as will be apparent to those of skill in the art in view of the disclosure herein.

Figure 13:
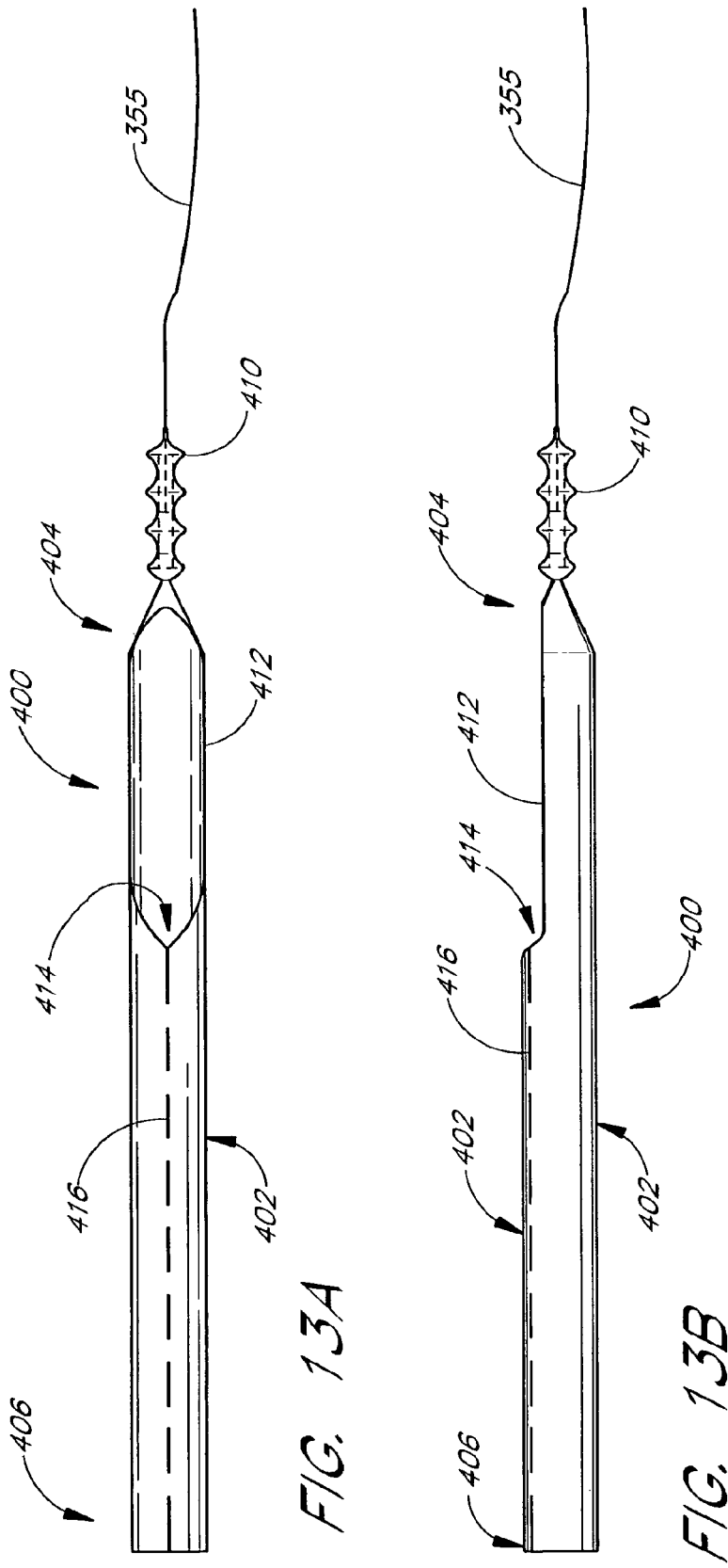
FIGS. 13A and B are top and side views of a peelable cover for restraining a portion of the bifurcated graft.

As mentioned above, proximal retraction of the outer sheath 328 will uncover the aortic trunk portion 392 and release the contralateral branch 396. In one embodiment, the aortic trunk portion 392 remains compressed within a peelable sheath 400. Referring to FIGS. 13A and 13B, the peelable sheath 400 comprises a tubular body 402 having a proximal end 404 and a distal end 406. The peelable sheath 400 is secured to the aortic trunk release wire 355. The aortic trunk release wire 355, in the illustrated embodiment, is secured by way of a joint 410 to the proximal end 404 of the peelable sheath 400. As shown in FIG. 9A, the release wire 355 extends through the catheter 320 between the outer sheath 328 and the inner core 330 and the release wire port lumen 354 exiting the catheter 320 at the release wire port 344.

Preferably, the proximal end 404 of the peelable sheath 100 is provided with a leader 412 of sheath material to facilitate positioning the joint 410, as will be explained below. The peelable sheath 400 is preferably also provided with a peel start point 414 such as a slit, perforation, V-shaped cut, or otherwise as will be apparent to those of skill in the art in view of the disclosure herein. The peelable sheath 400 preferably further includes a perforation line 416, crease, recess or other tear facilitating modification extending axially there along to facilitate predictable tearing of the material. In the illustrated embodiment, the perforation line 416 comprises a series of slits that are about 2.0 millimeters long and separated by a distance of about 1.5 millimeters.

The peelable sheath 400 may be made from any of a variety of thin, tearable materials as will be apparent to those of skill in the art in view of the disclosure herein. Preferably, the material exhibits sufficient strength that it will restrain the self expandable aortic trunk portion 392 while at the same time maintaining a low cross sectional profile and also permitting tearing to occur with a minimal amount of traction required on the release wire 355. In one embodiment, the peelable sheath 400 comprises a PTFE tube having a wall thickness of about 0.012", an outside diameter of about 0.218" and a length from the peel start point 414 to the distal end 406 of about 10.0 cm. The overall length from the joint 410 to the distal end 406 is about 17.0 cm. Of course, specific dimensions may be optimized for any particular device as will be understood in the art. Other thin wall tearable materials may also be used, such as PET, HDPE, or PE.

Referring to FIG. 9C, the iliac branches 394 and 396 will also remain compressed within a first (ipsilateral) tubular sheath 411 and a second (contralateral) tubular sheath 412. The first tubular sheath 411 is configured to restrain the ipsilateral branch 394 of the graft 390 in the constrained configuration. The first tubular sheath 411 is adapted to be axially proximally removed from the ipsilateral branch 394, thereby permitting the branch to expand to its implanted configuration. In one embodiment, the first tubular sheath 411 comprises a thin walled PTFE extrusion having an outside diameter of about 0.215" and an axial length of about 7.5 cm. A proximal end 414 of the tubular sheath 411 is necked down such as by heat shrinking to secure the first tubular sheath 411 to the distal hypotube 376. In this manner, proximal withdrawal of the distal hypotube 376 will proximally advance the first tubular sheath 411 relative to the graft 390, thereby deploying the self expandable ipsilateral branch 394 of the graft 390.

The second tubular sheath 412 is secured to the contralateral guidewire 374, which extends outside the catheter 320 at a point 416 (see FIG. 9B), such as may be conveniently provided at the junction 386 between the outer tubular sheath 328 and the distal tip 358. In the illustrated embodiment, the contralateral guidewire 374 extends through the groove 372 provided in the distal tip 358 and described above. The second tubular sheath 412 is adapted to restrain the contralateral branch 396 of the graft 390 in the reduced profile. In one embodiment of the invention, the second tubular sheath 412 has an outside diameter of about 0.215" and an axial length of about 7.5 cm. In the loaded configuration (FIG. 9B), the second tubular sheath 412 can have a significantly smaller cross-section than the first tubular sheath 411, due to the presence of the hypotube 376 within the ipsilateral branch 394.

As mentioned above, the second tubular sheath 412 is secured at its proximal end to the contralateral guidewire 374. This may be accomplished through any of a variety of securing techniques, such as heat shrinking, adhesives, mechanical interfit and the like. In one embodiment, the contralateral guidewire 374 is provided with one or more knots or other diameter enlarging structures to provide an interference fit with the proximal end of the second tubular sheath 412, and the proximal end of the second tubular sheath 412 is heat shrunk and/or bonded in the area of the knot to provide a secure connection. The same attachment structure can be used for the peelable sheath 400 as well. Any of a variety of other techniques for providing a secure connection between the corresponding wire and the tubular sheath can readily be used in the context of the present invention as will be apparent to those of skill in the art in view of the disclosure herein. The contralateral guidewire 374 and release wire 355 can comprise any of a variety of structures, including polymeric monofilament materials, braided or woven materials, metal ribbon or wire, or conventional guidewires as are well known in the art.

Figure 14:
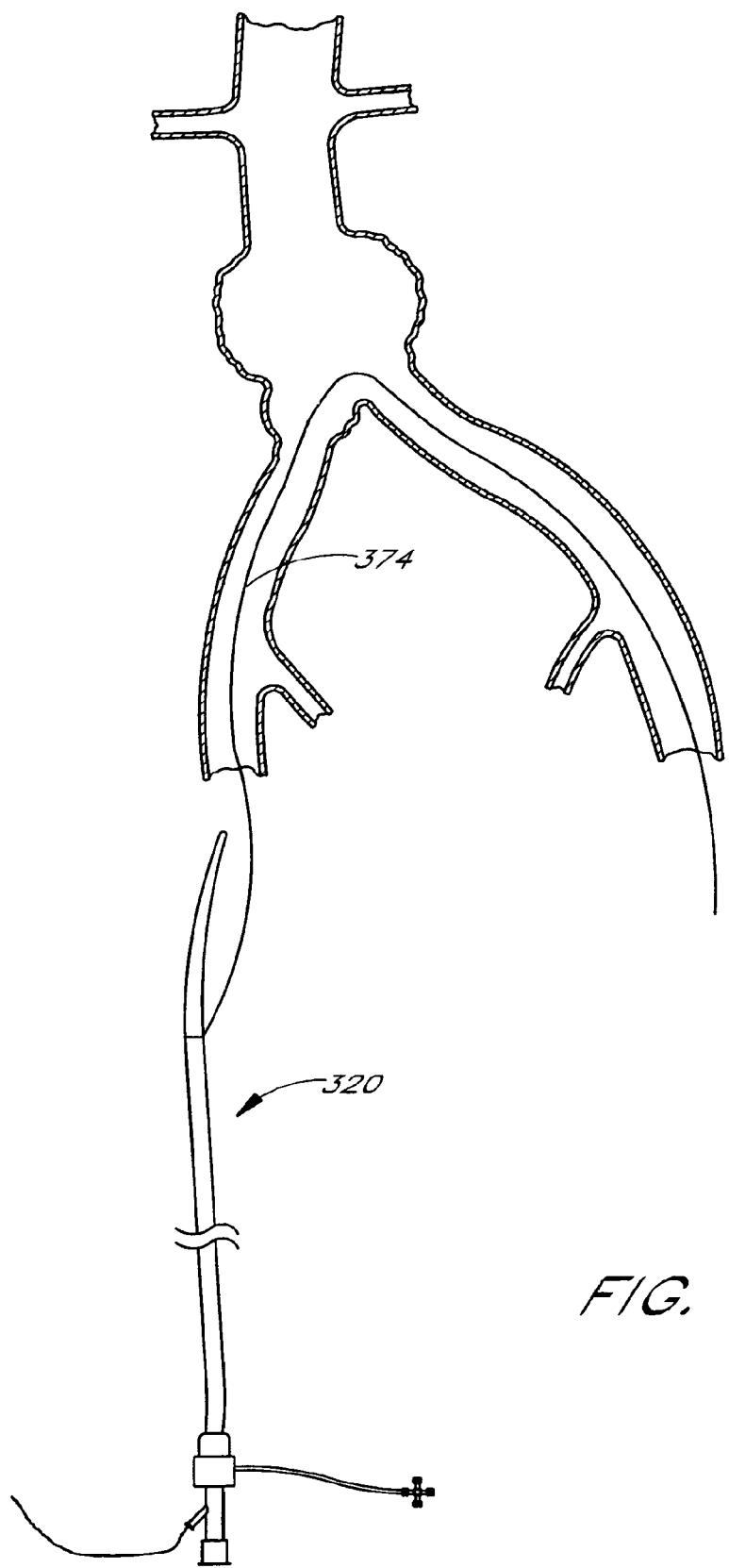
FIG. 14 is a schematic representation of a bifurcated graft deployment catheter of the present invention before being inserted into the ipsilateral iliac and the aorta, with the contralateral guidewire positioned within the contralateral iliac

Referring to FIG. 14, in use, the free end of the contralateral guidewire 374 is percutaneously inserted into the arterial system, such as at a first puncture in a femoral artery. The contralateral guidewire 374 is advanced through the corresponding iliac towards the aorta, and crossed over into the contralateral iliac in accordance with cross over techniques, which are well known in the art. The contralateral guidewire 374 is then advanced distally down the contralateral iliac where it exits the body at a second percutaneous puncture site.

Figure 15:
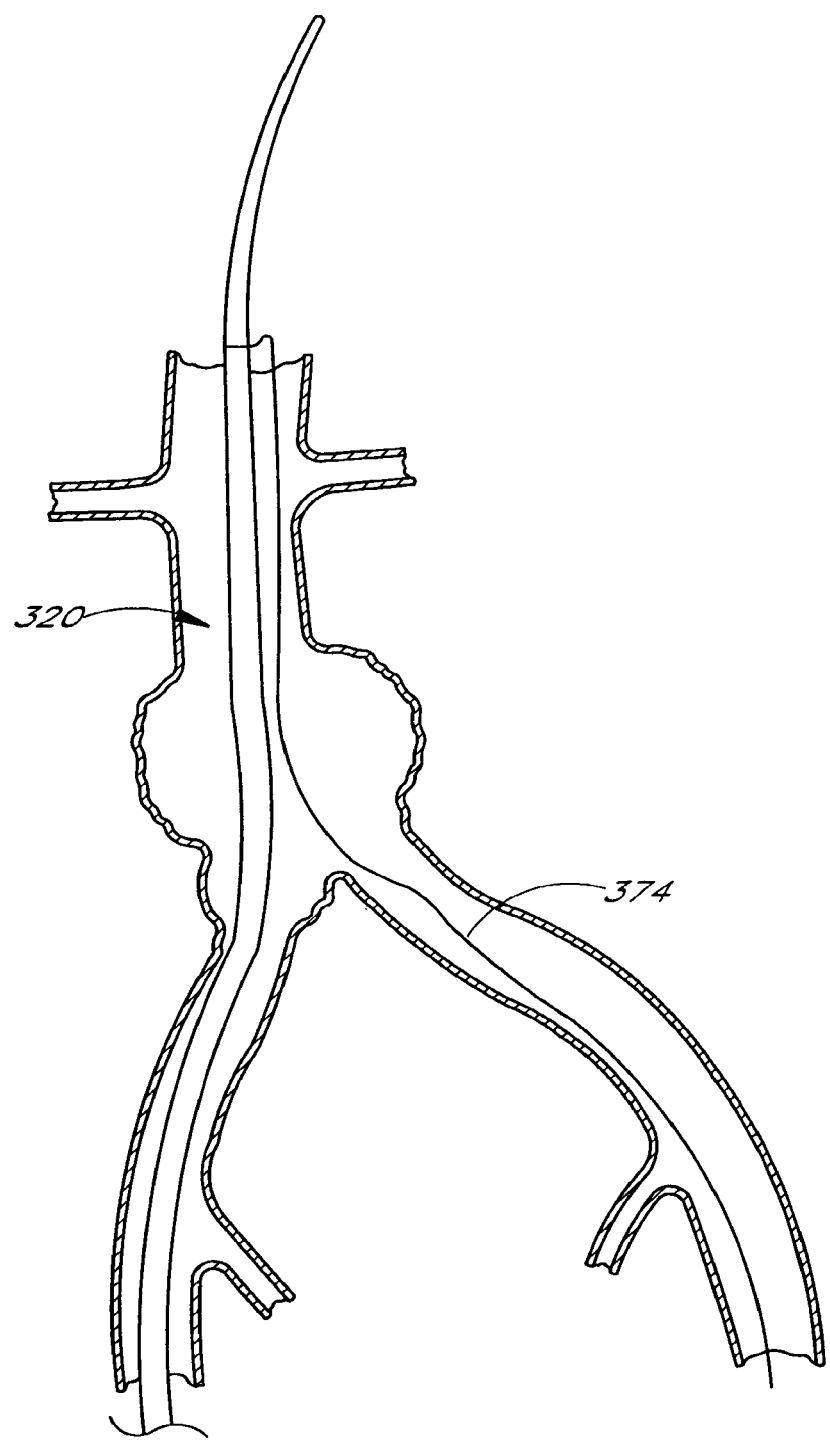
FIG. 15 is a schematic representation of a bifurcated graft deployment catheter of the present invention, positioned within the ipsilateral iliac and the aorta, with the contralateral guidewire positioned within the contralateral iliac.
Figure 16:
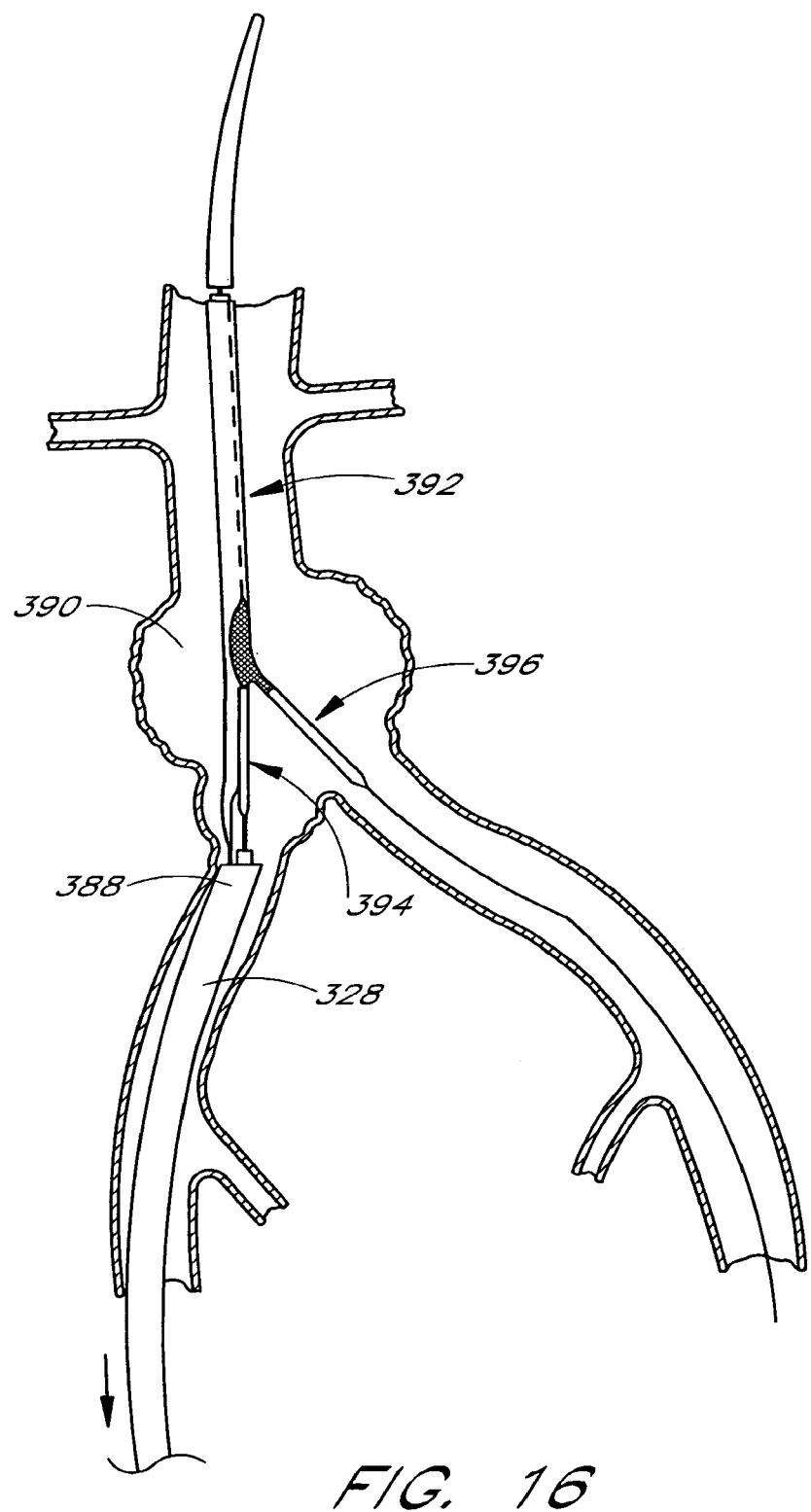
FIG. 16 is a schematic representation as in FIG. 15, with the outer sheath proximally retracted and the compressed iliac branches of the graft moving into position within the iliac arteries.

The catheter 320 is thereafter percutaneously inserted into the first puncture, and advanced along a guidewire (e.g. 0.035 inch) through the ipsilateral iliac and into the aorta. As the deployment catheter 320 is transluminally advanced, slack produced in the contralateral guidewire 374 is taken up by proximally withdrawing the contralateral guidewire 374 from the second percutaneous access site. In this manner, the catheter 320 is positioned in the manner generally illustrated in FIG. 15. Referring to FIG. 16, the outer sheath 328 is proximally withdrawn while generally maintaining the axial position of the overall deployment catheter 320, thereby exposing the aortic trunk 392 and releasing the first and second iliac branches 394, 396 of the graft 390.

Figure 17:
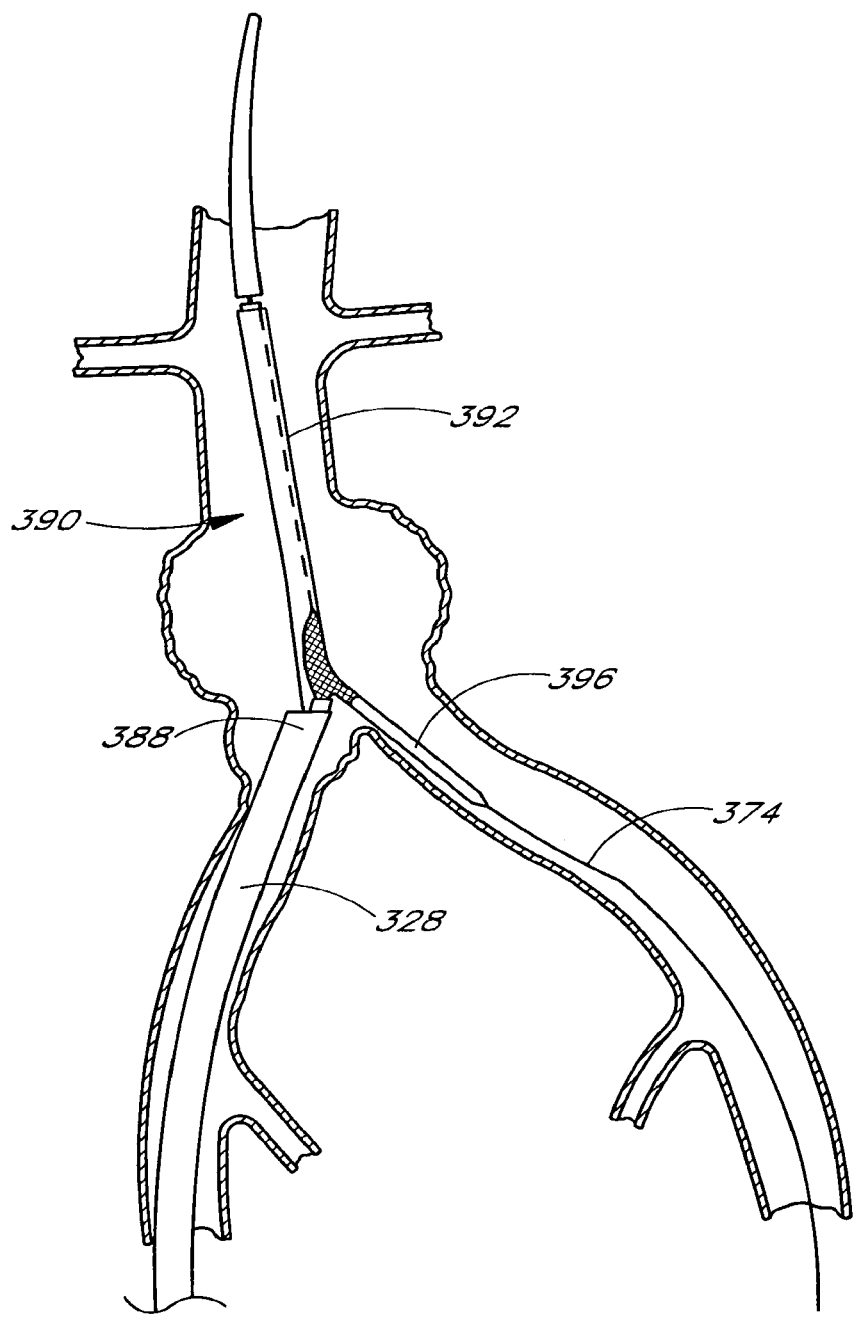
FIG. 17 is a schematic representation as in FIG. 16, with the outer sheath distally moved as compared to FIG. 16 so as to support the graft within the bifurcation.
Figure 18:
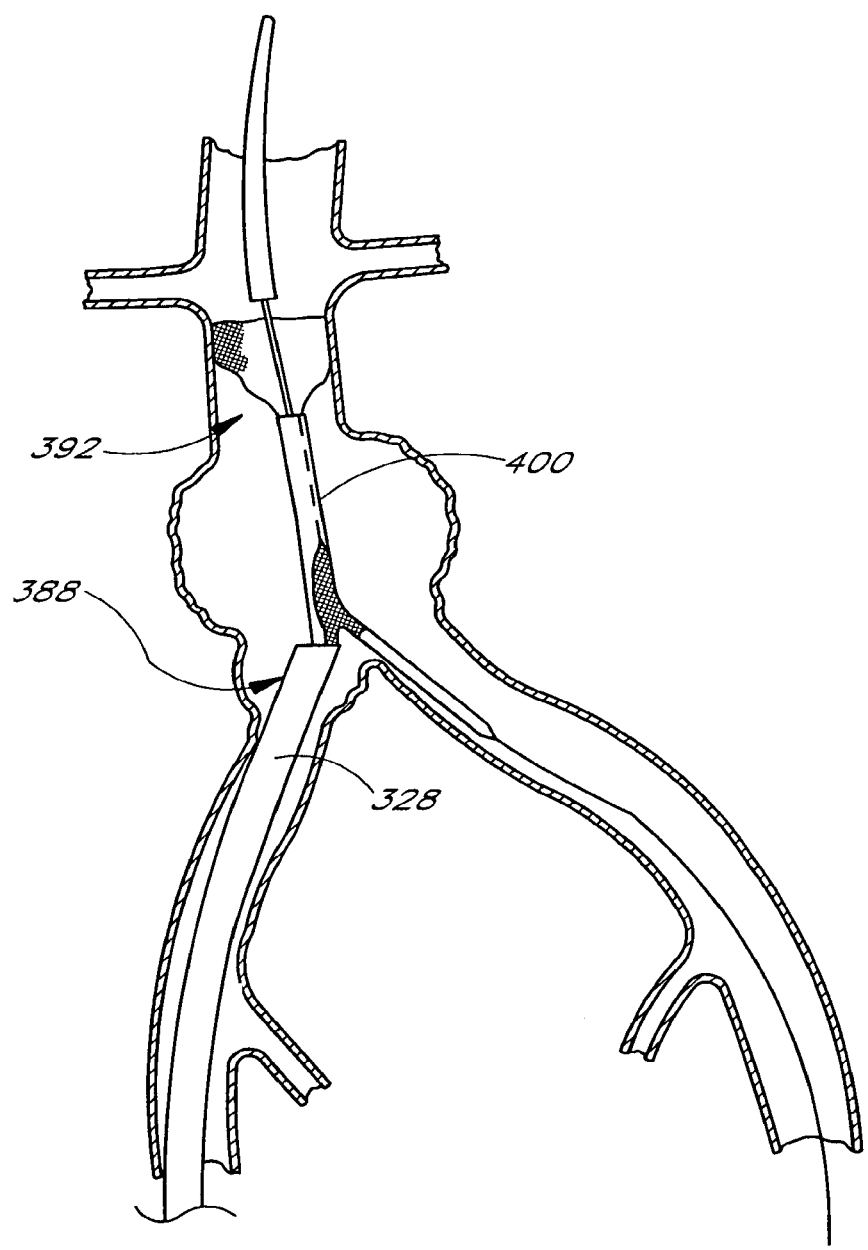
FIG. 18 is a schematic representation as in FIG. 17, with the main aortic trunk of the graft partially deployed within the aorta.
Figure 19:
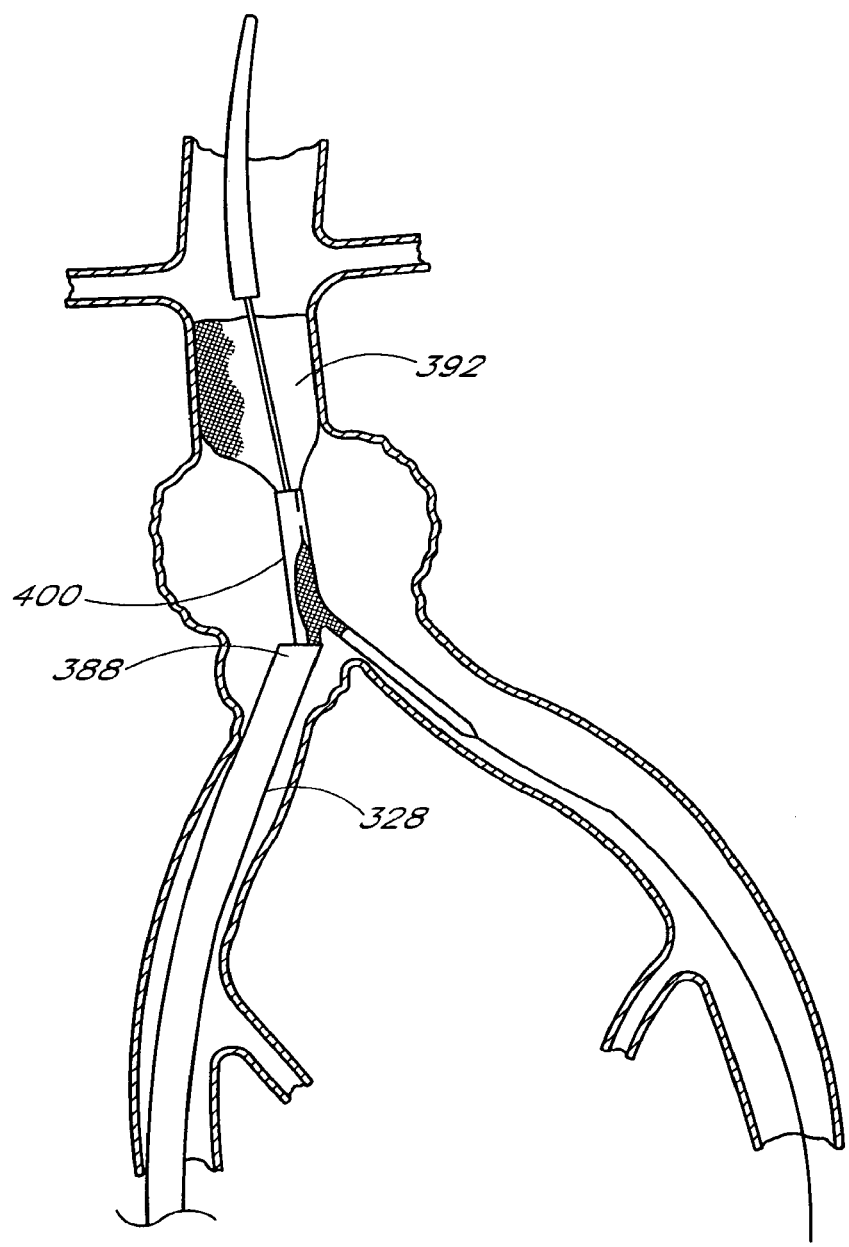
FIG. 19 is a schematic representation as in FIG. 18, with the main aortic trunk of the graft more fully deployed within the aorta.
Figure 20:
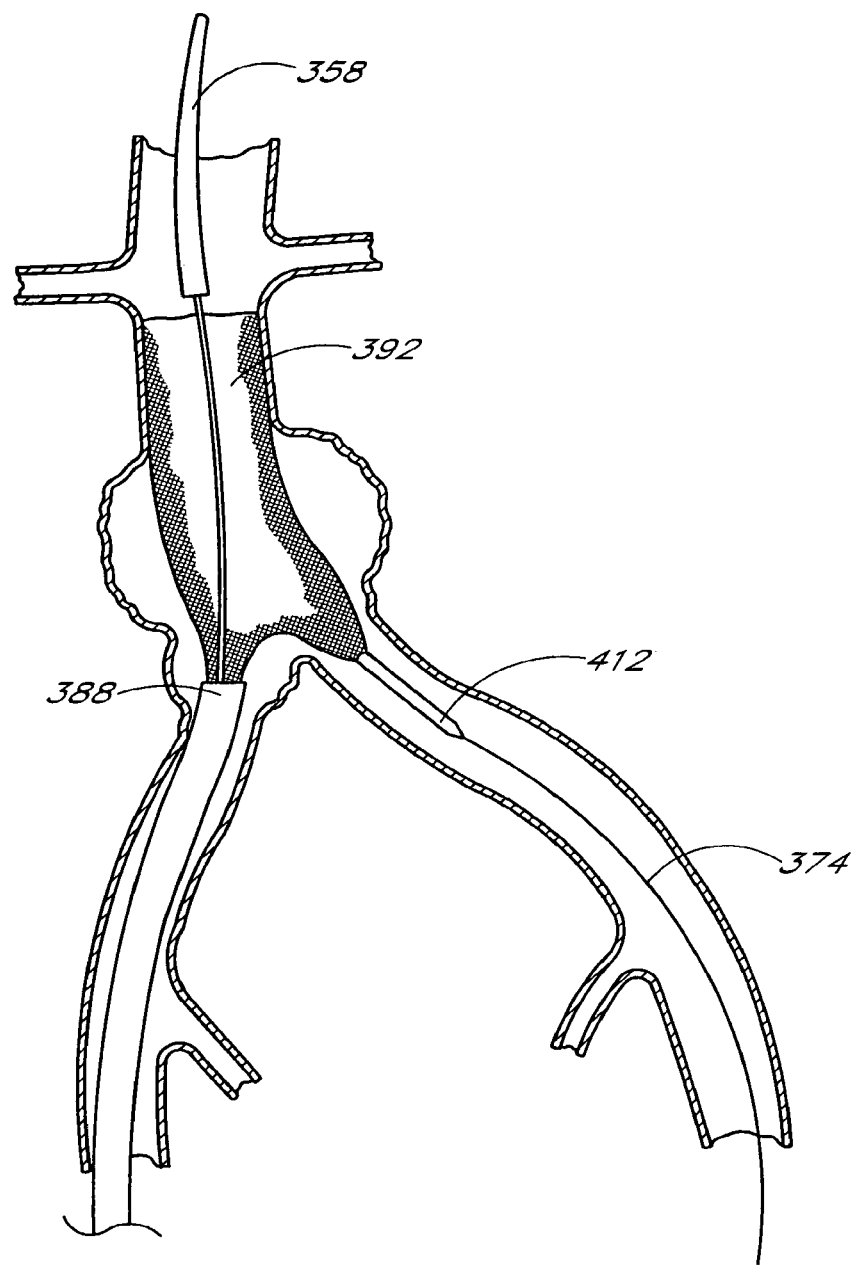
FIG. 20 is a schematic representation as in FIG. 19, with the main aortic trunk of the graft fully deployed within the aorta.

Referring to FIG. 17, the outer sheath 328 can be distally advanced and contralateral guidewire 374 withdraw so as to position the iliac position the branches 394, 396 of the graft 390 within the iliac arteries as illustrated. In this embodiment, the outer sheath 328 also provides support for the ispsilateral branch 394. Referring to FIG. 18, proximal traction is applied to the aortic trunk release wire 355. In the illustrated embodiment, the distal end 388 of the outer sheath 328 provides a fulcrum for minimizing injury to the adjacent tissue as proximal traction is applied to the aortic trunk release wire 355. Proximal retraction of the release wire 355 pulls the peelable sheath 400 down into the outer sheath 328. As shown in FIG. 19, retraction of the release wire 355 pulls the peelable sheath 400 proximally along the aortic trunk 392 such that the aortic trunk 392 is released from the distal end first. Further proximal retraction of the release wire 410 causes the peelable sheath 400 to tear or split distally thereby permitting complete retraction of the peelable sheath 400 from the aortic trunk 392 as illustrated in FIG. 20.

Following deployment of the aortic trunk 392, the contralateral guidewire 374 is thereafter proximally withdrawn, thereby by proximally withdrawing the second sheath 412 from the contralateral iliac branch 396 of the graft 390. See FIG. 21. The contralateral branch 396 of the graft 390 thereafter self expands to fit within the contralateral iliac artery. The guidewire 374 and sheath 412 may thereafter be proximally withdrawn and removed from the patient, by way of the second percutaneous access site.

Figure 21:
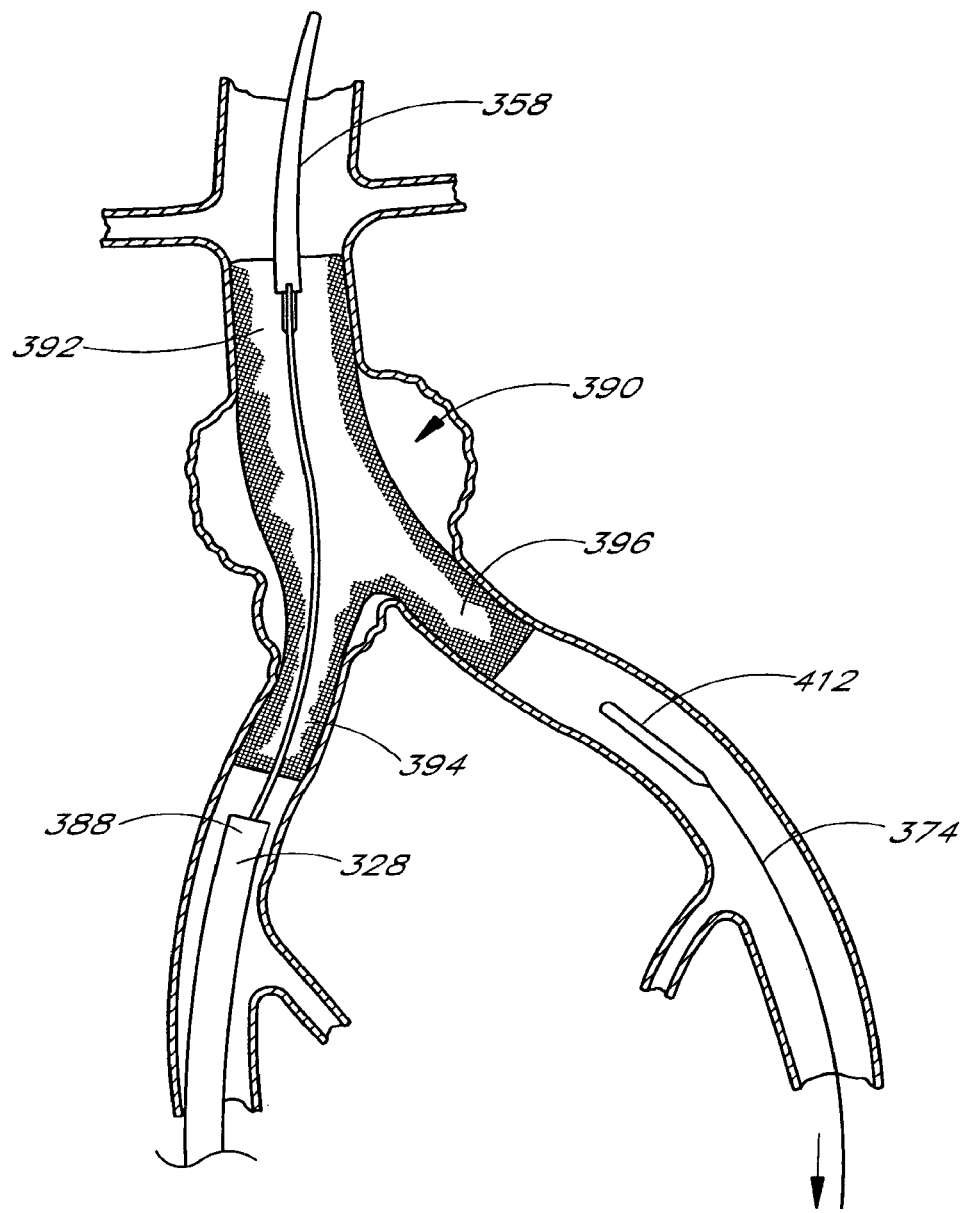
FIG. 21 is a schematic representation as in FIG. 20, with both of the contralateral and ipsilateral iliac branches of the graft deployed.
Figure 22:
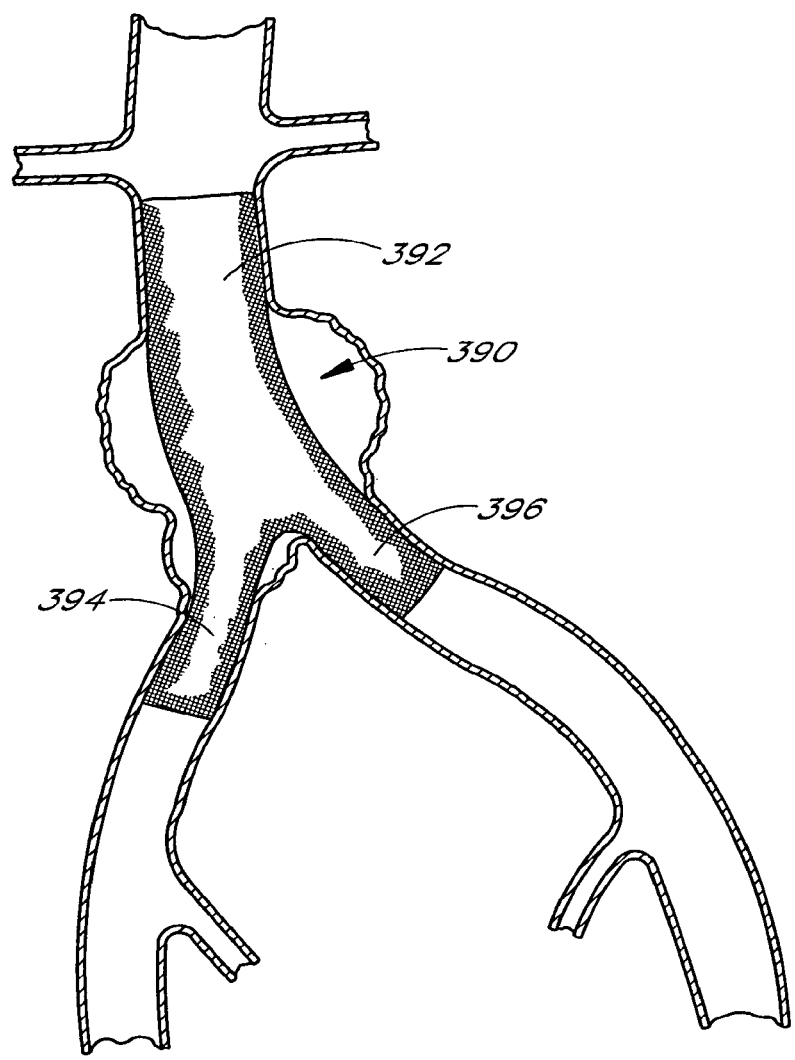
FIG. 22 is a schematic representation as in FIG. 21, following removal of the deployment catheter.

Thereafter, the outer sheath 328 may be proximally withdrawn to expose the ipsilateral branch 394 of the graft 390. As shown in FIG. 21, following deployment of the ipsilateral branch 386 of the graft 390, a central lumen through the aortic trunk 392 is sufficiently large to permit proximal retraction of the distal tip 358 through the deployed graft 390. As such, the inner core 330 may be proximally withdrawn to release the ipsilateral branch 394 from the first tubular sheath 411. Following deployment of the ipsilateral branch 394, the central lumen through the aortic trunk 392 and ipsilateral branch 394 is sufficiently large to permit complete proximal retraction of the deployment catheter 320 through the graft 390. As shown in FIG. 22, the graft 390 is now fully deployed and the deployment catheter 230 may thereafter be proximally withdrawn from the patient by way of the first percutaneous access site.

Figure 23:
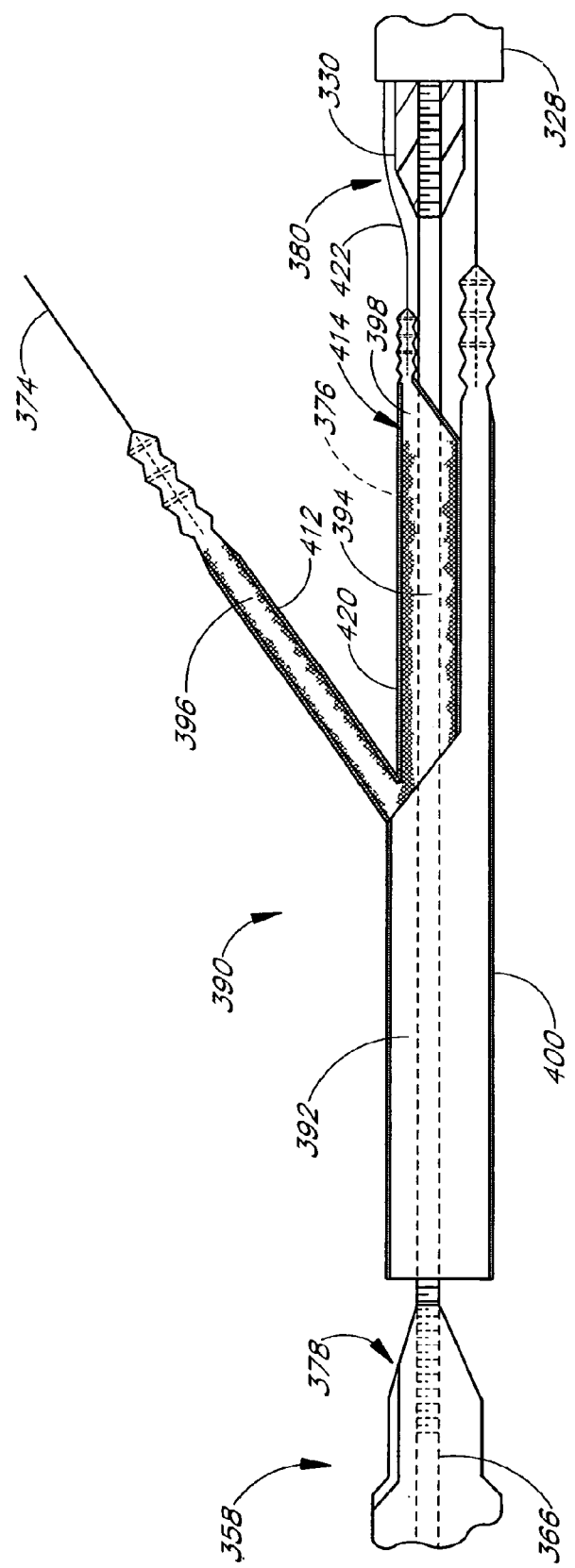
FIG. 23 is a cross-sectional side view of a modified embodiment of a bifurcation graft delivery system with the bifurcation graft delivery catheter shown in a stent exposed configuration.

Another technique, which has certain features and advantages according to the present invention, for deploying a self expandable bifurcation graft will now be described with reference to FIG. 23.

In this embodiment, the ipsilateral branch 394 is compressed within a second peelable sheath 420, which preferably is configured in a manner similar to the peelable sheath 410 described above. The second peelable sheath 420 is secured to an ipsilateral branch release wire 422, which as with the aortic trunk release wire 410 can extend proximally through the catheter 320 between the outer sheath 328 and the inner core 330. The ipsilateral branch release wire 422 can exit the catheter 320 through the release wire port 344 (see FIG. 9A). Of course, in a modified embodiment, a second release port can be provided.

In one embodiment, the ipsilateral branch 394 is released by proximally withdrawing the ipsilateral branch release wire 422 after the aortic trunk 392 and the contralateral branch 396 of the graft 390 have been released as described above. In such an arrangement, the second peelable sheath 420 is preferably not secured to the inner core 330. As such, releasing the ipsilateral branch 394 does not require proximal movement of the inner core 330. In one embodiment, the distal end 374 of the outer sheath 328 can be used to provide a fulcrum for minimizing injury to the adjacent tissue as proximal traction is applied to the release wire 422.

Figure 24:
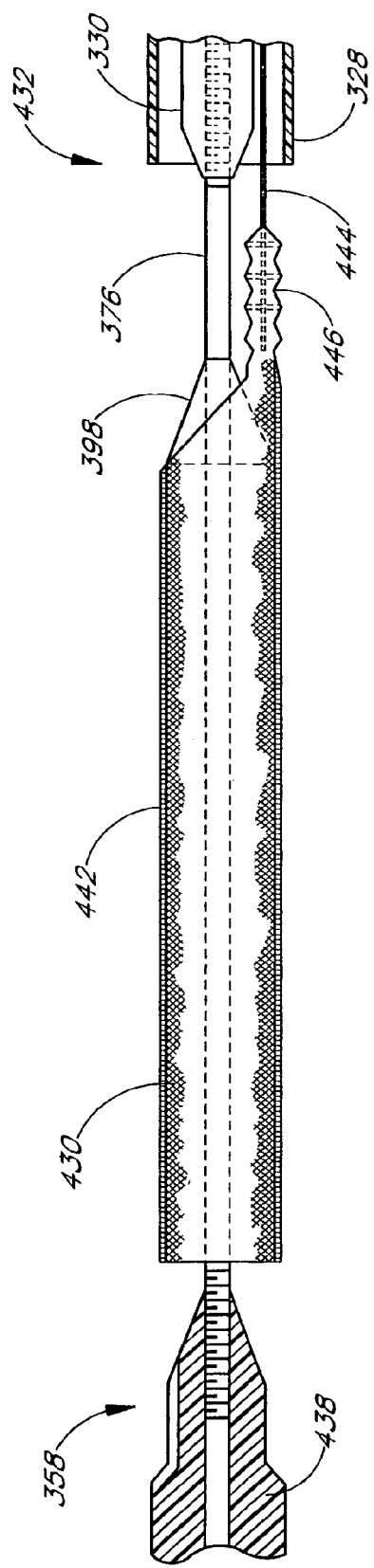
FIG. 24 is a cross-sectional view of a portion of a straight tube graft delivery system.

Certain aspects of the techniques describe above can also be used to deploy a self expandable straight tube graft. Such a straight tube graft is described in U.S. Pat. No. 6,197,049, the contents of which are hereby incorporated by reference herein. Such a technique, which has certain features and advantages according to the present invention, for deploying a self expandable straight tube graft 430 will now be described with reference to FIGS. 24 and 25.

In the illustrated embodiment, a deployment catheter 432 is configured in a manner substantially similar to the catheter 320 described above. As such, like numbers are used to refer to parts similar to those of FIGS. 9A-C. The illustrated catheter 432 includes an outer sheath 328, inner core 330 and a distal tip 358. The inner core 330 is connected to a distal tip 358 through a hypotube 376, which includes a proximal stop 398 for preventing proximal movement of the graft 430 on the hypotube 376. The graft 430 is positioned on the hypotube 376. In the loaded configuration (not shown), the outer sheath 328 covers the graft 430.

The graft 430 is compressed within a peelable sheath 442, which preferably is configured in a manner similar to the peelable sheath 410 described above. The peelable sheath 442 is secured to a release wire 444 through a joint 446. The release wire 444 preferably extends through the catheter 432 between the outer sheath 328 and the inner core 330.

In use, the catheter 432 is percutanously inserted into a first puncture in the femoral artery and advanced along a guide wire through the ipsilateral iliac and into the aorta. Once the catheter 432 is in the proper position, the outer sheath 328 can proximally withdrawn while maintaining the general axial position of the catheter 432, thereby exposing the graft 430. The graft 430 is released by proximally withdrawing the release wire 444. After the graft 430 is released, the central lumen through the graft 430 is sufficiently large to permit complete proximal retraction of the distal tip 438. The catheter 432 may thereafter be proximally withdrawn from the patient by way of the first access site.

Figure 25:
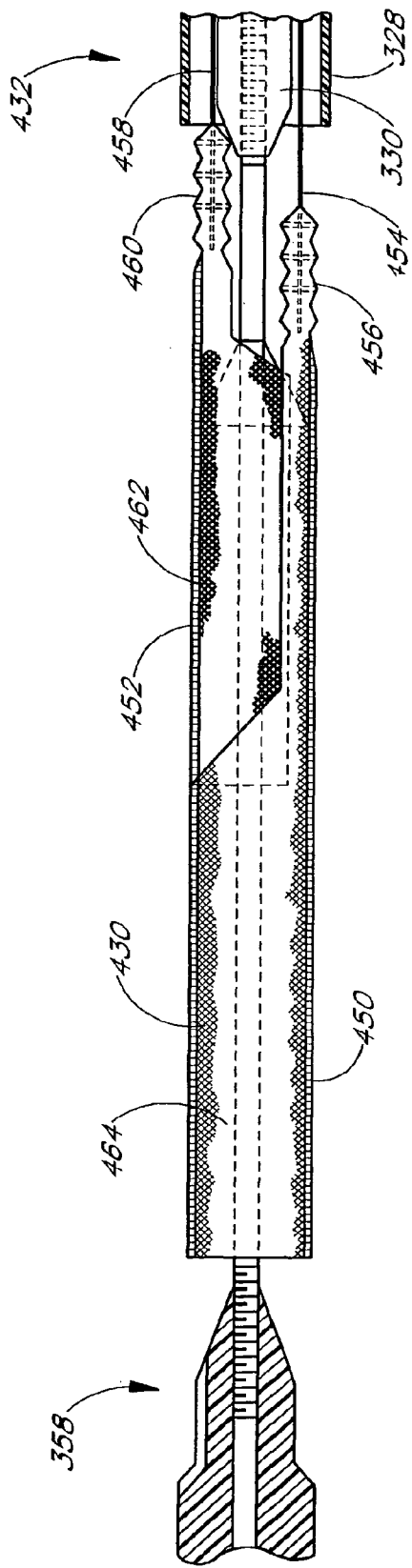
FIG. 25 is a cross-sectional view of a portion of a modified embodiment of a straight tube graft delivery system.

Referring to FIG. 25, another modified embodiment of a technique for deploying a self expandable straight tube graft 430 is illustrated. In this embodiment, the straight tube graft 430 is compressed with a distal peelable sheath 450 and a proximal peelable sheath 452, which are configured in a manner similar to the peelable sheaths described above. The distal peelable sheath 450 is attached to a distal release wire 454 through a junction 456 and in a similar manner the proximal peelable sheath 452 is attached to a proximal release wire 458 through a junction 460.

After the catheter 432 is in position, the outer sheath 328 is proximally withdrawn while maintaining the general axial position of the catheter 432, thereby exposing the graft 430. A device proximal (anatomically inferior) portion 462 of the graft 130 is then released by proximally withdrawing the proximal release wire 458. After the proximal portion 462 of the graft 430 is released, the distal portion 464 of the graft is released by proximally withdrawing the distal release wire 454. Preferably, the distal portion 464 is released after the proximal portion 462 so as to prevent a "sail" effect in the thoracic area due to the high pressure, although release can be accomplished in the reverse order.

Once the graft 430 has been deployed, the central lumen through the graft is sufficiently large to permit complete proximal retraction of the distal tip 358. The catheter 432 may thereafter be proximally withdrawn from the patient by way of the first access site. The forgoing two step deployment structure can also be utilized on the main aorta portion of a bifurcation graft, if deployment anatomically distal to proximal is preferred over the previously disclosed anatomically proximal to distal. See, e.g., FIGS. 17-19.

As the catheter 320, 432 is transluminally advanced along the guidewire through the ipsilateral iliac and into the aorta, it is advantageous for the surgeon to be able to visualize the position of the distal end 388 of the outer sheath 328 so as to be able to more accurately place the graft within the patient. Catheters may be conventionally formed from extruded PTFE and/or PEEK, which are transparent under fluoroscopic visualization. To aid the visualization of the catheter, the distal end 388 of the outer sheath 329 preferably includes a band 500 of any of a variety of radio opaque ("RO") materials that are well known in the art as shown in FIGS. 26A and 26B. In the illustrated embodiment, the distal end 388 of the outer catheter 328 is provided with a groove 352, in which the band 500 is positioned. In a modified embodiment, the distal end 388 can be formed without the groove 352 and the band 500 can be bonded directly around the outer sheath 328.

Figure 27A:
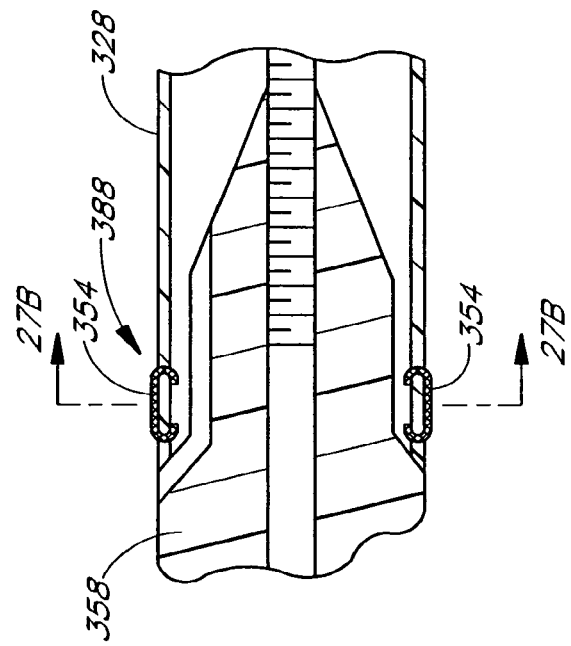
FIG. 27A is a modified embodiment of the portion shown in FIG. 26A.
Figure 27B:
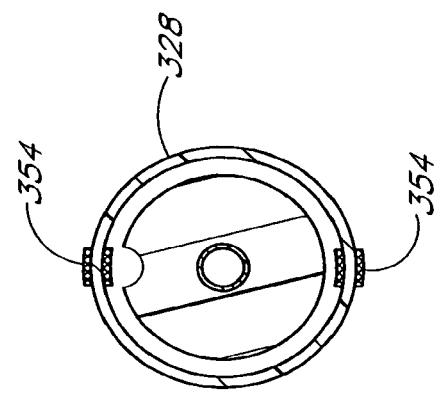
FIG. 27B is a cross-sectional view taken through line 27B-27B of FIG. 26A.
Figure 28B:
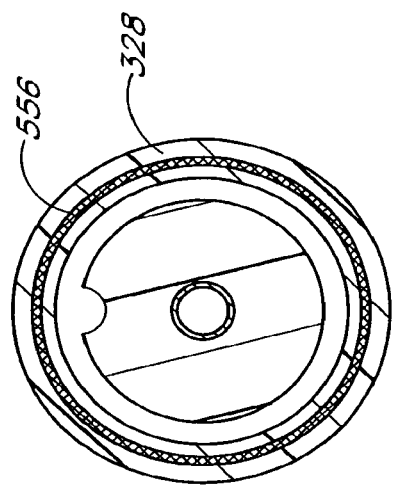
FIG. 28B is a cross-sectional view taken through line 28B-28B of FIG. 26A
Figure 28A:
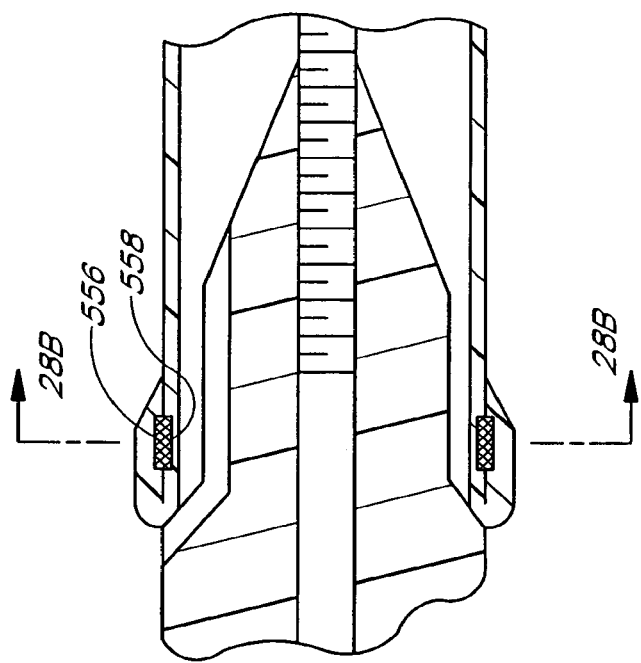
FIG. 28A is another modified embodiment of the portion shown in FIG. 26A.
Figure 29B:
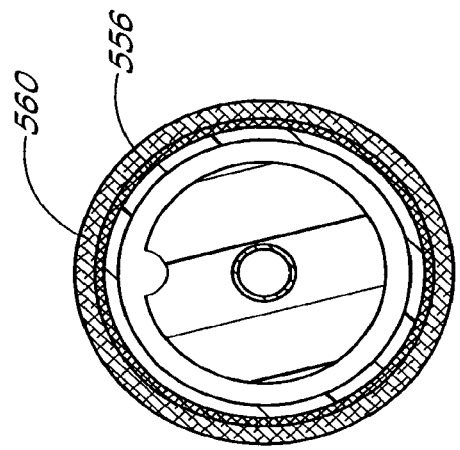
FIG. 29B is a cross-sectional view taken through line 29B-29B of FIG. 26A.
Figure 29A:
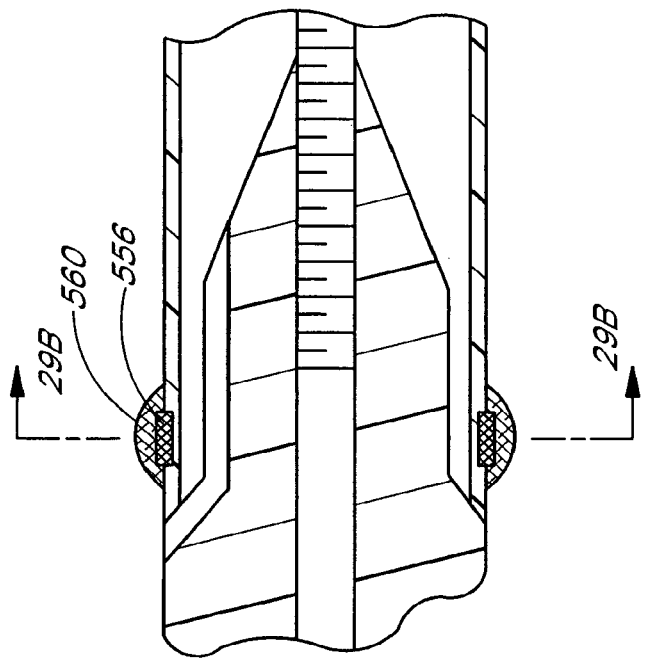
FIG. 29A is still another modified embodiment of the portion shown in FIG. 26A.

FIGS. 27A and 27B illustrate another embodiment for providing RO material on the catheter. In this embodiment, RO fixtures or staples 354 are inserted through the outer sheath 328 at the distal end 388. FIGS. 28A and 28B illustrate yet another embodiment for providing RO material on the catheter. In this embodiment, the distal end 388 of the outer sheath 328 includes a band 556 of RO material that is positioned on the sheath 328 or within a groove 558. The distal end 388 of the outer sheath 328 is inverted proximally over the band 556 so as to cover the outer surface of the band. The outer sheath 328 may then be thermally bonded or adhesively bonded to itself proximal the marker bands 556, to enclose the marker band 556. In the embodiment shown FIGS. 29A and 29B, the band 556 is covered by a layer 560 of shrink wrap tubing, epoxy or similar material. In other embodiments, RO material can be dispersed in the PEEK or PTFE material, which forms the body of the catheter. In such an embodiment, the density of the RO material is preferably higher at the distal end 388 of the outer sheath 328. In still other embodiments, the RO material can be attached to or dispersed within the distal tip 358 and/or the inner core 330 in a manner similar to that described above.

While a number of variations of the invention have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A method for deploying a bifurcated endoluminal prosthesis at the junction of a main vessel and first and second branch vessels, comprising:
   providing a deployment system containing a prosthesis having a main body section and first and second proximally extending branch sections;
   introducing the deployment system into the first branch vessel at a first access site;
   advancing the deployment system distally through at least a portion of the first branch vessel and into the main vessel;
   releasing the second branch section of the prosthesis by proximally retracting an outer sheath of the deployment system;
   expanding the main body section of the prosthesis from a radially compressed state within the deployment system to a radially expanded state within the main vessel by removing a first peelable sheath from the main branch section; and
   expanding the second branch section within the second branch vessel by proximally retracting a second branch release wire.

2. The method of claim 1, wherein the second branch release wire is proximally retracted through a second access site.

3. The method of claim 1, further comprising expanding the first branch section within the first branch vessel by proximally retracting an inner core of the deployment system.

4. The method of claim 1, further comprising expanding the first branch section within the first branch vessel by removing a second peelable sheath from the first branch section.

5. The method claim 4, wherein the second peelable sheath is removed by proximally retracting a first branch release wire.

6. The method of claim 1, wherein the main vessel is an aorta and the first and second branch vessels are ipsilateral and contralateral iliac arteries.

7. The method of claim 1, wherein the second branch section comprises a self-expandable wire support.

8. The method claim 1, wherein the first peelable sheath is removed by proximally retracting a main branch release wire through the first access site.

9. A method for deploying a straight tube endoluminal prosthesis, comprising:
   providing a deployment system containing a straight tube prosthesis including a distal section and a proximal section;
   introducing the deployment system into a vessel at an access site;
   advancing the deployment system distally through the vessel;
   proximally retracting an outer sheath of the deployment system to expose the prosthesis; and
   expanding at least a portion of the prosthesis from a radially compressed state within the deployment system to a radially expanded state within the vessel by proximately retracting a first release element so as to tear a peelable cover.

10. The method of claim 9, wherein expanding at least a portion of the prosthesis includes expanding the distal portion of the prosthesis.

11. The method of claim 10, further comprising expanding a proximal portion of the prosthesis from a radially compressed state within the deployment system to a radially expanded state within the vessel by proximately retracting a second release element so as to tear a second peelable cover.

* * * * *

UNITED STATES PATENT AND TRADEMARK OFFICE
CERTIFICATE OF CORRECTION

PATENT NO. : 8,568,466 B2  
APPLICATION NO. : 13/269332  
DATED : October 29, 2013  
INVENTOR(S) : Shaolian et al.

Page 1 of 1

It is certified that error appears in the above-identified patent and that said Letters Patent is hereby corrected as shown below:

In the Specification

In column 4 at line 42, Change "iliac" to --iliac.--.
In column 5 at line 19, Change "26A" to --26A.--.
In column 5 at line 46, Change "prosthesis," to --prosthesis.--.
In column 6 at line 41, Change "and or" to --and/or--.
In column 8 at line 47, Change "slideable" to --slidable--.
In column 12 at line 37, Change "polymide" to --polyamide--.
In column 15 at line 7, Change "ispsilateral" to --ipsilateral--.
In column 16 at line 31, Change "percutanously" to --percutaneously--.

In the Claims

In column 18 at line 25, In Claim 5, Change "method claim" to --method of claim--.
In column 18 at line 33, In Claim 8, Change "method claim" to --method of claim--.

Signed and Sealed this
Twenty-seventh Day of May, 2014

Michelle K. Lee
*Deputy Director of the United States Patent and Trademark Office*